United States Patent
Shih et al.

(10) Patent No.: US 7,041,682 B2
(45) Date of Patent: May 9, 2006

(54) NK$_1$ ANTAGONISTS

(75) Inventors: Neng-Yang Shih, North Caldwell, NJ (US); Steven Wang, Jersey City, NJ (US); Gregory Reichard, Ann Arbor, MI (US); Dong Xiao, Warren, NJ (US); Cheng Wang, Summit, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/612,176

(22) Filed: Jul. 2, 2003
(Under 37 CFR 1.47)

(65) Prior Publication Data
US 2004/0072867 A1 Apr. 15, 2004

Related U.S. Application Data

(60) Provisional application No. 60/393,708, filed on Jul. 3, 2002.

(51) Int. Cl.
*A61K 31/445* (2006.01)
*C07D 211/56* (2006.01)

(52) U.S. Cl. ............ 514/326; 546/207; 546/208; 546/209; 546/210; 546/212; 546/214; 544/124

(58) Field of Classification Search ........ 514/326; 546/207, 208, 209, 210, 212, 214; 544/124
See application file for complete search history.

(56) References Cited

U.S. PATENT DOCUMENTS

| 5,620,989 A * | 4/1997 | Harrison et al. ........... 514/317 |
| 5,760,018 A * | 6/1998 | Baker et al. ................ 514/63 |
| 2003/0158173 A1 * | 8/2003 | Paliwal et al. ........ 514/210.02 |

FOREIGN PATENT DOCUMENTS

| WO | WO 94/10165 | 5/1994 |
| WO | WO 95/19344 | 7/1995 |

OTHER PUBLICATIONS

Starykh et al. Relation of structure . . . CA 65:6503 (1966).*
Ikizler et al. "Synthesis and biological activity . . . " CA 129:260395 (1998).*
Johnson et al. "A tachykinin receptor antagonist . . . " CA 125:339038 (1996).*
Harrison et al. "preparation of . . . " CA 122:304898 (1995).*
Patani et al. "Bioisosterim; a rational approach in drug design" Che, Rev. 96 3147-76 (1996).*
Al-Sehemi et al "Kinetic resolution of amines . . . " CA 137:5741 (2002).*
Tavorath et al. "Drug treatment of chemotherapy induced delayed emesis" CA 126:205 (1996).*
McAllister et al. "GR205171 blocks apomorphine . . . " CA 129:254773 (1998).*
Reid et al. "Comparison of the neurokinin-1 antagonist . . . " CA 134:95359 (2000).*
Campos et al. "Prevention of cisplatin-induced emesis . . . " CA 135:190161 (2001).*
Patent Cooperation Treaty International Search Report, PCT/US/03/20783 (CN01576K)—International Filing Date Feb. 7, 2003—3 Pages.

* cited by examiner

*Primary Examiner*—Celia Chang
(74) *Attorney, Agent, or Firm*—Thomas A. Blinka

(57) ABSTRACT

Disclosed are NK$_1$ antagonists having the formula:

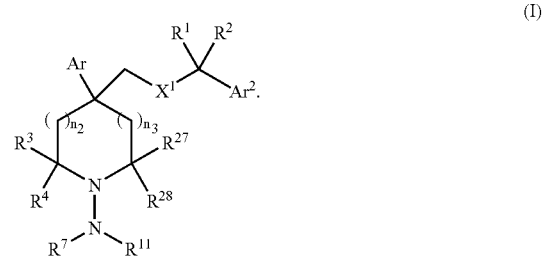

Also disclosed are methods for treating a number of physiological disorders, symptoms or diseases, including emesis, depression, anxiety and cough, using the compounds of formula (I).

20 Claims, No Drawings

NK₁ ANTAGONISTS

REFERENCE TO RELATED APPLICATION

This application claims the benefit of U.S. Provisional Application Ser. No. 60/393,708 filed Jul. 3, 2002, the disclosure of which is incorporated herein by reference thereto.

BACKGROUND OF THE INVENTION

This invention relates to antagonists of the neuropeptide neurokinin-1 ($NK_1$ or NK-1) receptor, compositions containing the antagonists, and methods of using the antagonists for the treatment of various diseases and conditions, including emesis, depression, anxiety and cough.

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors have been studied to potentially treat or prevent various mammalian disease states. For instance, $NK_1$ receptors have been reported to be involved in microvascular leakage and mucus secretion. Representative types of neurokinin receptor antagonists and the disorders that can be treated with them include, for example, sleep, pain, migraine, emesis, nociception and inflammation, see, for example, U.S. Pat. No. 6,329,401, U.S. Pat. No. 5,760,018, U.S. Pat. No. 5,620,989, WO 95/19344, WO 94/13639, and WO 94/10165.

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases, while minimizing side effects. This invention provides such $NK_1$ antagonists.

SUMMARY OF THE INVENTION

This invention is directed to a compound of the formula (I):

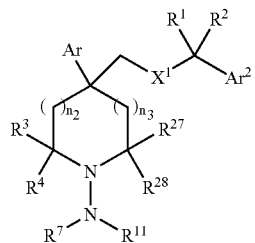

(I)

or a pharmaceutically acceptable salt or solvate thereof, wherein $Ar^1$ and $Ar_2$ are each independently selected from the group consisting of $(R^{19})_{n7}$-heteroaryl- and

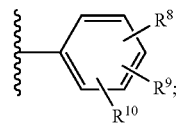

$X_1$ is selected from the group consisting of —O—, —S—, —SO—, —SO₂—, —$NR^{12}$—, —$N(COR^{12})$— and —$N(SO_2R^{15})$—;

$R^1$, $R^3$ and $R^5$ are each independently selected from the group consisting of H and $C_1$–$C_6$ alkyl;

$R^2$, $R^4$ and $R^6$ are each independently selected from the group consisting of H, —$CONR^{13}R^{14}$ and —$(CH_2)_{n1}$-G; wherein G is selected from the group consisting of H, —$CF_3$, —$CHF_2$, —$CH_2F$, —OH, —O—($C_1$–$C_6$) alkyl, —$SO_2R^{13}$, —O—($C_3$–$C_8$ cycloalkyl), —$NR^{13}R^{14}$, —$SO_2NR^{13}R^{14}$, —$NR^{13}SO_2R^{15}$, —$NR^{13}COR^{12}$, —$NR^{12}(CONR^{13}R^{14})$, $CONR^{13}R^{14}$, —$COOR^{12}$ and $C_3$–$C_8$ cycloalkyl; or $R^1$ and $R^2$, taken together with the carbon to which they are attached, form a $C_3$–$C_6$ cycloalkyl ring; or $R^1$ and $R^2$, taken together with the carbon to which they are attached, form a

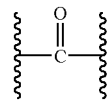

group, provided that X1 is —O— or —$NR^{12}$ when said

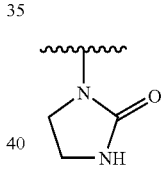

is formed; or $R^3$ and $R^4$, taken together with the carbon to which they are attached, form a

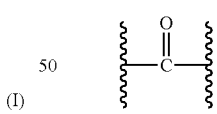

group; or $R^5$ and $R^6$, taken together with the carbon to which they are attached, form a

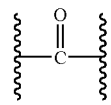

group;

$R^7$ and $R^{11}$ are each independently selected from the group consisting of H, $C_1$–$C_6$ alkyl, $C_3$–$C_8$ cycloalkyl, $(R^{16})_{n7}$-aryl-, $(R^{19})_{n7}$-heteroaryl-, —COOR$^{29}$, —CONR$^{21}$R$^{22}$, —CON(R$^{21}$)(CH$_2$)$_n$-G$^1$, —S(O)$_{n5}$(CH$_2$)$_n$-G$^1$, —S(O)$_{n5}$R$^{13}$, —CO(CH$_2$)$_n$- G$^1$ and —(CH$_2$)$_{n1}$-G$^1$;
wherein
n is 0–4, and
G$^1$ is selected from the group consisting of H, —OH, (C$_1$–C$_6$)alkyl, —O—(C$_1$–C$_6$ alkyl), —S(O)$_{n5}$R$^{13}$, —O—(C$_3$–C$_8$ cycloalkyl), —NR$^{13}$R$^{14}$, —SO$_2$NR$^{13}$R$^{14}$, —NR$^{13}$SO$_2$R$^{15}$, —NR$^{13}$COR$^{12}$, —NR$^{12}$(CONR$^{13}$R$^{14}$), —OC(=O)R$^{12}$, —CONR$^{13}$R$^{14}$, —COOR$^{12}$, C$_3$–C$_8$ cycloalkyl, —CF$_3$, $(R^{16})_{n7}$-aryl-O—, $(R^{16})_{n7}$-aryl-, $(R^{19})_{n7}$-heteroaryl-, $(R^{19})_{n7}$-heterocycloalkyl- and alkenyl (e.g., —CH=CH$_2$, and —CH$_2$—CH=CH$_2$), and
provided that, when n is 0, then G$^1$ is selected from the group consisting of H, (C$_1$–C$_6$)alkyl, alkenyl, —CONR$^{13}$R$^{14}$, —COOR$^{12}$, C$_3$–C$_8$ cycloalkyl, —CF$_3$, $(R^{16})_{n7}$-aryl-, $(R^{19})_{n7}$-heteroaryl-, and $(R^{19})_{n7}$-heterocycloalkyl-; and
provided that, when n, is 1, then G$^1$ is selected from the group consisting of H, (C$_1$–C$_6$)alkyl, alkenyl, —S(O)$_{n5}$R$^{13}$, —SO$_2$NR$^{13}$R$^{14}$, —CONR$^{13}$R$^{14}$, —COOR$^{12}$, C$_3$–C$_8$ cycloalkyl, —CF$_3$, $(R^{16})_{n7}$-aryl-, $(R^{19})_{n7}$-heteroaryl- wherein said heteroaryl ring is bound by a ring carbon to the —(CH$_2$)$_{n1}$— group, and $(R^{19})_{n7}$-heterocycloalkyl- wherein said heterocycloalkyl ring is bound by a ring carbon to the —(CH$_2$)$_{n1}$— group; or
R$^7$ and R$^{11}$, taken together with the nitrogen to which they are attached, form a 5–7 membered heterocycloalkyl ring of the following formula:

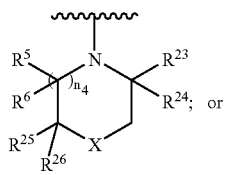

R$^7$ and R$^{11}$, taken together with the nitrogen to which they are attached, form a 5-membered ring having the formula (A) or (B):

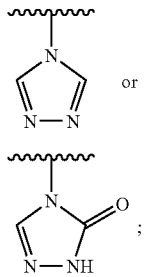

X is selected from the group consisting of —NR$^{20}$—, —N(CONR$^{13}$R$^{14}$)—, —N(CO$_2$R$^{13}$)—, —N(SO$_2$R$^{15}$)—, —N(COR$^{12}$)—, —N(SO$_2$NHR$^{13}$)—, —O—, —S—, —SO—, —SO$_2$—, —CF$_2$—, —CH$_2$—, and —C(R$^{12}$)F—;

R$^8$, R$^9$ and R$^{10}$ are each independently selected from the group consisting of H, C$_1$–C$_6$ alkyl, C$_3$–C$_8$ cycloalkyl, —OR$^{12}$, halogen, —CN, —NO$_2$, —CF$_3$, —CHF$_2$, —CH$_2$F, —OCF$_3$, —OCHF$_2$, —OCH$_2$F, —COOR$^{12}$, —CONR$^{21}$R$^{22}$, —NR$^{21}$COR$^{12}$, —NR$^{21}$CO$_2$R$^{15}$, —NR$^{21}$CONR$^{21}$R$^{22}$, —NR$^{21}$SO$_2$R$^{15}$, —NR$^{21}$R$^{22}$, —SO$_2$NR$^{21}$R$^{22}$, —S(O)$_{n5}$R$^{15}$, (R$_{16}$)$_{n7}$-aryl- and $(R^{19})_{n7}$-heteroaryl-;

R$^{12}$ is selected from the group consisting of H, C$_1$–C$_6$ alkyl and C$_3$–C$_8$ cycloalkyl;

R$^{13}$ and R$^{14}$ are each independently selected from the group consisting of H, C$_1$–C$_6$ alkyl, C$_2$–C$_3$ alkyl-O—CH$_3$, C$_3$–C$_8$ cycloalkyl, $(R^{19})_{n7}$-aryl(CH$_2$)$_{n6}$— and $(R^{19})_{n7}$-heteroaryl-(CH$_2$)$_{n6}$—; or R$^{13}$ and R$^{14}$, taken together with the nitrogen to which they are attached, form a 4–7 membered ring containing from 0–3 additional heteroatoms selected from the group consisting of —O—, —S— and —NR$^{12}$—;

R$^{15}$ is C$_1$–C$_6$ alkyl, C$_3$–C$_8$ cycloalkyl or —CF$_3$;

R$^{16}$ is 1 to 3 substituents each independently selected from the group consisting of C$_1$–C$_6$ alkyl, C$_3$–C$_8$ cycloalkyl, C$_3$–C$_6$ alkoxy, halogen and —CF$_3$;

R$^{19}$ is 1 to 3 substituents each independently selected from the group consisting of C$_1$–C$_6$ alkyl, C$_3$–C$_8$ cycloalkyl, —OH, halogen, —CN, —NO$_2$, —C(O)CF$_3$, —CF$_3$, —CHF$_2$, —CH$_2$F, —OCF$_3$, —OCHF$_2$, —OCH$_2$F, —O—(C$_1$–C$_6$ alkyl), —C—(C$_3$–C$_8$ cycloalkyl), —COOR$^{12}$, —CONR$^{21}$R$^{22}$, —NR$^{21}$R$^{22}$, —NR$^{21}$COR$^{12}$, —NR$^{21}$CO$_2$R$^{12}$, —NR$^{21}$CONR$^{21}$R$^{22}$, —NR$^{21}$SO$_2$R$^{15}$ and —S(O)$_{n5}$R$^{15}$;

R$^{20}$ is H, C$_1$–C$_6$ alkyl, C$_3$–C$_8$ cycloalkyl, —(CH$_2$)$_{n6}$-heterocycloalkyl, $(R^{19})_{n7}$-aryl(CH$_2$)$_{n6}$— or $(R^{19})_{n7}$-heteroaryl-(CH$_2$)$_{n6}$—;

R$^{21}$ and R$^{22}$ are each independently selected from the group consisting of H, C$_1$–C$_6$ alkyl, C$_3$–C$_8$ cycloalkyl and benzyl; or R$^{21}$ and R$^{22}$, taken together with the nitrogen to which they are attached, form a 4–7 membered heteroaryl ring containing from 0–3 additional heteroatoms selected from the group consisting of —O—, —S— and —NR$^{12}$—;

R$^{23}$ and R$^{24}$ are each independently selected from the group consisting of H, C$_1$–C$_6$ alkyl and —CONR$^{13}$R$^{14}$; or R$^{23}$ and R$^{24}$, taken together with the carbon atom to which they are attached, form a

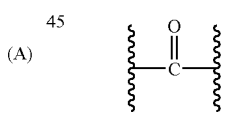

group;

R$^{25}$, R$^{26}$, R$^{27}$ and R$^{28}$ are each independently selected from the group consisting of H and C$_1$–C$_6$ alkyl; or R$^{25}$ and R$^{26}$, taken together with the carbon atom to which they are attached, form a

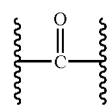

group; or

R$^{27}$ and R$^{28}$, taken together with the carbon atom to which they are attached, form a

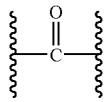

group;

$R^{29}$ is selected from the group consisting of $C_1$–$C_6$ alkyl and $C_3$–$C_8$ cycloalkyl;

$n_1$ is 1–4;

$n_2$ and $n_3$ are each independently 0–3, provided that a sum of $n_2$ and $n_3$ is 0–4;

$n_4$ is 0–2;

$n_5$ is 0–2;

$n_6$ is 0–3; and $n_7$ is 0–3; and provided that, when $n_4$ is 0, and $R^{25}$ and $R^{26}$ are each H, then X is not —O—, —$NR^{20}$— or —S—.

This invention is also directed to a pharmaceutical composition comprising an effective amount of at least one (e.g., one) compound of formula (I) and a pharmaceutically acceptable carrier.

This invention is also directed to a method for effecting an $NK_1$ receptor in a patient comprising administering to said patient an effective amount of at least one (e.g., one) compound of formula (I).

This invention is also directed to a method for treating an $NK_1$ receptor mediated disease (i.e., a disease associated with an $NK_1$ receptor, or a disease involving an $NK_1$ receptor in part of the disease process) in a patient in need of such treatment comprising administering to said patient an effective amount of at least one (e.g., one) compound of formula (I).

This invention is also directed to a method of treating a disease (or disorder or condition) in a patient in need of such treatment, wherein said disease is selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmological disorders (e.g., retinitis, ocular hypertension and cataracts), (4) central nervous system conditions, such as depressions (e.g., neurotic depression), anxieties (e.g., general anxiety, social anxiety and panic anxiety disorders), phobias (e.g., social phobia), and bipolar disorder, (5) addictions (e.g., alcohol dependence and psychoactive substance abuse), (6) epilepsy, (7) nociception, (8) psychosis, (9) schizophrenia, (10) Alzheimer's disease, (11) AID's related dementia, (12) Towne's disease, (13) stress related disorders (e.g., post tramautic stress disorder), (14) obsessive/compulsive disorders, (15) eating disorders (e.g., bulemia, anorexia nervosa and binge eating), (16) sleep disorders, (17) mania, (18) premenstrual syndrome, (19) gastrointestinal disorders (e.g., irritable bowel syndrome, Crohn's disease, colitis, and emesis), (20) atherosclerosis, (21) fibrosing disorders (e.g., pulmonary fibrosis), (22) obesity, (23) Type II diabetes, (24) pain related disorders (e.g., headaches, such as migraines, neuropathic pain, post-operative pain, and chronic pain syndromes), (25) bladder and genitourinary disorders (e.g., interstitial cystitis and urinary incontinence), (26) emesis (e.g., chemotherapy-induced (e.g., induced by cisplatin, doxorubicin, and taxane), radiation-induced, motion sickness, ethanol-induced, and post operative nausea and vomiting), and (27) nausea, comprising administering to said patient an effective amount of at least one (e.g., one) compound of formula (I).

This invention is also directed to a method of treating a disease (or disorder or condition) in a patient in need of such treatment, wherein said disease is selected from the group consisting of: respiratory diseases (e.g., cough), depression, anxiety, phobia, bipolar disorder, alcohol dependence, psychoactive substance abuse, nociception, psychosis, schizophrenia, stress related disorders, obsessive/compulsive disorder, bulemia, anorexia nervosa, binge eating, sleep disorders, mania, premenstrual syndrome, gastrointestinal disorders, obesity, pain related disorders (e.g., headaches, such as migraines, neuropathic pain, post-operative pain, and chronic pain syndromes), bladder disorders, genitourinary disorders, emesis and nausea, comprising administering to said patient an effective amount of at least one (e.g., one) compound of formula (I).

This invention is also directed to a method of treating a disease wherein there is microvascular leakage and mucus secretion in a patient in need of such treatment, comprising administering to said patient an effective amount of at least one (e.g., one) compound of formula (I).

This invention is also directed to a method of treating asthma, emesis, nausea, depressions, anxieties, cough and pain related disorders in a patient in need of such treatment comprising administering to said patient an effective amount of at least one (e.g., one) compound of formula (I).

This invention is also directed to a method of treating emesis, depression, anxiety and cough in a patient in need of such treatment comprising administering to said patient an effective amount of at least one (e.g., one) compound of formula (I).

This invention is also directed to a method for antagonizing an effect of a Substance P at a neurokinin-1 receptor site in a patient in need of such treatment, comprising administering to said patient at least one (e.g., one) compound of formula (I).

This invention is also directed to a method for the blockade of neurokinin-1 receptors in a patient in need of such treatment, comprising administering to said patient at least one (e.g., one) compound of formula (I).

This invention is also directed to a method for treating depression and/or anxiety in a patient in need of such treatment comprising administering to said patient an effective amount of one or more (e.g., one) compounds of formula (I) in combination with an effective amount of one or more (e.g., one) anti-depressant agents and/or one or more (e.g., one) anti-anxiety agents.

This invention is also directed to a method of treating an $NK_1$ receptor mediated disease in a patient in need of such treatment comprising administering to said patient an effective amount of one or more (e.g., one) compounds of formula (I) in combination with an effective amount of one or more (e.g., one) selective serotonin reuptake inhibitors ("SSRIs").

This invention is also directed to a method of treating depression and/or anxiety in a patient in need of such treatment comprising administering to said patient an effective amount of one or more (e.g., one) compounds of formula (I) in combination with an effective amount of one or more (e.g., one) selective serotonin reuptake inhibitors.

This invention is also directed to a method of treating an $NK_1$ receptor mediated disease in a patient in need of such treatment comprising administering to said patient an effective amount of at least one (e.g., one) compound of formula (I) in combination with at least one (e.g., one) therapeutic agent selected from the group consisting of: other types of NK$_1$ receptor antagonists (e.g., those that are disclosed in the neurokinin receptor antagonist patents cited in the above Background Section), prostanoids, H$_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, ET$_A$ antagonists, renin inhibitors, serotonin 5-HT$_3$ receptor antagonists (e.g., ondansetron), serotonin 5-HT$_{2c}$ receptor agonists, nociceptin receptor agonists, glucocorticoids (e.g., dexamethasone), rho kinase inhibitors, potassium channel modulators and inhibitors of multi-drug resistance protein 5.

This invention is also directed to a method for treating an NK$_1$ mediated disease in a patient in need of such treatment comprising administering to said patient an effective amount of a compound of formula (I) in combination at least one (e.g., one) therapeutic agent selected from the group consisting of: prostanoids, such as prostaglandin E$_1$; α-adrenergic agonists, such as phentolamine mesylate; dopamine receptor agonists, such as apomorphine; angiotensin II antagonists, such as losartan, irbesartan, valsartan and candesartan; ET$_A$ antagonists, such as bosentan and ABT-627; serotonin 5-HT$_3$ receptor antagonists, such as ondansetron; and glucocorticoids, such as dexamethasone.

This invention is also directed to a method for treating an NK$_1$ mediated disease in a patient in need of such treatment comprising administering to said patient an effective amount of at least one (e.g., one) compound of formula (I) in combination with and effective amount of at least one (e.g., one) therapeutic agent selected from the group consisting of: other types of NK$_1$ receptor antagonists, SSRIs, dopamine receptor agonists, serotonin 5-HT$_3$ receptor antagonists, serotonin 5-HT$_{2c}$ receptor agonists, nociceptin receptor agonists, glucocorticoids and inhibitors of multi-drug resistance protein 5.

This invention is also directed to a method for treating emesis, nausea and/or vomiting in a patient in need of such treatment comprising administering to said patient an effective amount of at least one (e.g., one) compound of formula (I) in combination with and effective amount of at least one (e.g., one) serotonin 5-HT$_3$ receptor antagonist (e.g., ondansetron) and/or at least one glucocorticoid (e.g., dexamethasone).

DETAILED DESCRIPTION OF THE INVENTION

Except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

(Boc) is tert-butoxy carbonyl.
(Boc)$_2$O is di-tert-butyl dicarbonate.
CBS is (S)-methyloxazaborolidine, a Corey-Bakshi-Shibata catalyst (described in E. S. Corey, R. K. Bakshi and S. Shibata, *J. Am. Chem. Soc.*, 109, 7925 (1987)).
CBZ is carbonylbenzyloxy (i.e., —C(O)OCH$_2$C$_6$H$_5$).
CDI is carbonyldiimidazole.
DBU is 1,8-diazabicyclo[5.4.0]un dec-7-ene.
DCC is 1,3-dicyclohexylcarbodiimide.
DIBAL or DIBAL-H is diisobutylaluminum hydride.
DIEA is diisopropylethyl amine.
DMAP is dimethylaminopyridine.
DMSO is dimethylsulfoxide.
EDC is 1-(3-dimethylaminopropyl)-3-ethycarbodiimide HCl.
HOBT is hydroxybenzotriazole.
Ph represents phenyl.
TEMPO is a free radical of 2, 2, 6, 6-tetra methyl-1-piperidinyloxy.
THF is tetrahydrofuran.
TLC is thin layer chromatography.
TMSCI is chlorotrimethylsilane.

"At least one", examples include 1–3, 1–2 or 1.
"Heteroatom" means a nitrogen, sulfur or oxygen atom. Multiple heteroatoms in the same group may be the same or different.
"One or more", examples include 1–3, 1–2 or 1.
"Patient" includes mammals (e.g., humans) and non-mammals.
"Alkyl" means a substituted or unsubstituted, straight or branched saturated hydrocarbon chain having the designated number of carbon atoms. Where the number of carbon atoms is not specified, 1 to 20 carbons are intended. Preferred alkyl groups contain 1 to 12 carbon atoms in the chain. More preferred alkyl groups contain 1 to 6 carbon atoms in the chain. Non-limiting examples of suitable alkyl groups include methyl, ethyl, n-propyl, isopropyl, n-butyl, t-butyl, n-pentyl, heptyl, nonyl, decyl, fluoromethyl and trifluoromethyl.
"Alkoxy" means an —O-alkyl group. Representative alkoxy groups include methoxy, ethoxy and isopropoxy.
"Aryl" means a substituted or unsubstituted, aromatic, mono- or bicyclic, carbocyclic ring system having from one to two aromatic rings. The aryl moiety will generally comprise from 6 to 14 carbon atoms, preferably 6 to 10 carbon atoms, with all available substitutable carbon atoms of the aryl moiety being intended as possible points of attachment. Representative examples include phenyl, tolyl, xylyl, cumenyl, naphthyl, indanyl, indenyl, and the like. The carbocyclic ring can optionally be substituted with from one to five, preferably one to three, moieties, such as mono- through pentahalo, alkyl, trifluoromethyl, phenyl, hydroxy, alkoxy, phenoxy, amino, monoalkylamino, dialkylamino, and the like, said moieties being independently selected.
"Cycloalkyl" or "cycloalkane" means an unsubstituted or substituted, saturated, stable, non-aromatic, carbocyclic ring, having, preferably, from three to fifteen carbon atoms, more preferably, from three to eight carbon atoms. The cycloalkyl ring may be fused with one to three cycloalkyl, aromatic (e.g., benzofused), heterocyclic or heteroaromatic rings. The cycloalkyl may be attached at any endocyclic carbon atom that results in a stable structure. Preferred carbocyclic rings have from five to six carbons. Examples of cycloalkyl rings include cyclopropyl, cyclobutyl, cyclopentyl, cyclohexyl, cycloheptyl, and the like.
"Hal" or "halo" or "halogen" or "halide means a chloro, bromo, fluoro or iodo atom radical. Chlorides, bromides and fluorides are preferred halides.
"Heteroaryl" means an aromatic mono- or multi-cyclic ring system comprising about 5 to about 14 ring atoms, preferably about 5 to about 10 ring atoms, in which one or more of the ring atoms is an atom other than carbon, for example, nitrogen, oxygen or sulfur, i.e., the heteroaryl ring comprises one or more heteroatoms independently selected from nitrogen, oxygen and sulfur. Preferred heteroaryl rings comprise about 5 to about 6 ring atoms. Optionally, a nitrogen atom of a heteroaryl ring can be oxidized to the corresponding N-oxide. Representative heteroaryl (heteroaromatic) groups include pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, isothiazolyl, benzothiazolyl, benzoxazolyl, oxazolyl, pyrrolyl, isoxazolyl, 1,3,5-triazinyl and indolyl groups.

"Heterocycloalkyl" means an unsubstituted or substituted, saturated, mono- or multi-cyclic ring system comprising from three to fifteen members, and preferably, from three to ring atoms, wherein from 1–3 of said ring atoms are heteroatoms selected from the group consisting of —$NR^{30}$—, —O— and —S—, wherein $R^{30}$ is selected from the group consisting of H, $C_1$–$C_6$ alkyl, $C_3$–$C_8$ cycloalkyl and —$COCF_3$, said heterocycloalkyl ring being optionally substituted on the ring carbons with from 1 to 3 the substituents selected from the group consisting of $C_1$–$C_6$ alkyl, $C_3$–$C_8$ cycloalkyl, —OH, halogen, —CN, —$NO_2$, —C(O)$CF_3$, —$CF_3$, —$CHF_2$, —$CH_2F$, —$OCF_3$, —$OCHF_2$, —$OCH_2F$, —O—($C_1$–$C_6$ alkyl), —O—($C_3$–$C_8$ cycloalkyl), —$COOR^2$, —$CONR^{21}R^{22}$, —$NR^{21}R^{22}$, —$NR^{21}COR^{12}$, —$NR^{21}CO_2R^{12}$, —$NR^{21}CONR^{21}R^{22}$, —$NR^{21}SO_2R^{15}$ and —S(O)$_{n5}R^{15}$;

"Hydroxyalkyl" means an alkyl group having at least one hydroxy (e.g., one —OH) substituent. The alkyl group may also be substituted with other groups. Representative hydroxyalkyl groups include hydroxymethyl, hydroxyethyl and hydroxypropyl groups.

"Prodrug" represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems*, Vol. 14 of A.C.S. Symposium Series (1987), and in *Bioreversible Carriers in Drug Design*, E. B. Roche, ed., American Pharmaceutical Ass'n and Pergamon Press (1987), each of which is incorporated herein by reference thereto.

"Effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, and the particular active ingredient(s) being employed, and like factors within the knowledge and expertise of the attending physician.

Unless stated to the contrary, a substituent is bound to a structure through the last named moiety of the substituent. For example, an "arylalkyl" substituent is bound to a structure through the "alkyl" moiety of the substituent.

When a substituent occurs more than once in a formula (e.g., ($R^{16}$)$_{n7}$ wherein n7 is 2 or 3), each selection for each occurrence is made independently of the other selections, unless stated otherwise.

This invention is directed to compounds having the formula (I), including any and all isomers, such as enantiomers, stereoisomers, diastereomers, atropisomers, rotomers, and tautomers, and prodrugs of the compounds having the formula (I), and the isomers thereof, and their corresponding salts, solvates (e.g., hydrates), esters, and the like.

The invention is also directed to pharmaceutical compositions comprising one or more compounds of formula (I) and one or more pharmaceutically acceptable excipients/carriers, or salts, solvates, and esters thereof.

The compounds of formula (I) can be useful for treating a variety of diseases, symptoms and physiological disorders, such as emesis, depression, anxiety and cough. Thus, the invention is also directed to methods of treating such types of diseases, symptoms and disorders by administering to a patient in need of such treatment an effective amount of a pharmaceutical composition comprising at least one compound having the formula (I) and at least one pharmaceutically acceptable excipient/carrier.

Compounds having the formula (I) can have at least one asymmetrical carbon atom. All isomers, including stereoisomers, diastereomers, atropisomers, enantiomers, tautomers and rotational isomers, in pure form and mixtures, including racemic mixtures, are contemplated as being part of the invention. Prodrugs, salts, solvates, esters, etc., derived from the compounds having the formula (I), or precursors thereof, are also within the scope of the invention. The invention includes d- and l- isomers in pure form and in admixture, including racemic mixtures. Isomers can be prepared using conventional techniques, either by reacting optically pure or optically enriched starting materials or by separating isomers of a compound having the formula (I).

The inventive compounds can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

The inventive compounds may form pharmaceutically-acceptable salts with organic and inorganic acids. For example, pyrido-nitrogen atoms may form salts with strong acids, while compounds having basic substituents, such as amino groups, also form salts with weaker acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention. Acidic compounds of the invention (e.g., those compounds which possess a carboxyl group or a phenolic hydroxyl group) form pharmaceutically-acceptable salts with inorganic and organic bases. Representative examples of such types of salts are sodium, potassium, calcium, aluminum, gold and silver salts. Also included are salts formed with pharmaceutically-acceptable amines, such as ammonia, alkyl amines, hydroxyalkylamines, N-methylglucamine, and the like. Many such types of salts are known in the art, for example, those that are described in WO 87/05297, which is incorporated in its entirety by reference herein. Preferred cationic salts include alkali metal salts (e.g., sodium and potassium) and alkaline earth metal salts (e.g., magnesium and calcium). Preferred anionic salts include halide (e.g., chloride), acetate and phosphate salts.

All such acid and base salts are intended to be pharmaceutically acceptable salts within the scope of the invention, and all acid and base salts are considered equivalent to the free forms of the corresponding compounds for purposes of the invention.

In a preferred embodiment of the compounds of formula (I):

$X^1$ is —O—; and $Ar^1$ and $Ar^2$ are each independently

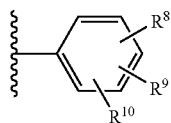

wherein $R^8$, $R^9$ and $R^{10}$ are as defined for formula (I).

In a more preferred embodiment of the compounds of formula (I):

$X^1$ is —O—; and $Ar^1$ and $Ar^2$ are each independently

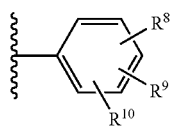

wherein $R^8$, $R^9$ and $R^{10}$ are each independently selected from the group consisting of H, —CH$_3$, halogen and CF$_3$;

$R^1$ is selected from the group consisting of H and CH$_3$; and $R^2$ is selected from the group consisting of H, CH$_3$ and CH$_2$OH.

Preferably, for the compounds of formula (I), $R^4$ is H, or $R^3$ and $R^4$, taken together with the carbon to which they are attached form the group

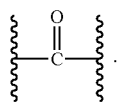

Preferably, for the compounds of formula (I), $R^7$ and $R^{11}$, taken together with the nitrogen to which they are attached, form a 5–7 membered heterocycloalkyl ring of the formula:

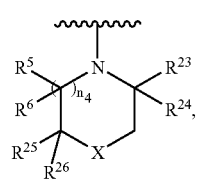

wherein X, $R^5$, $R^6$, $R^{23}$, $R^{24}$, $R^{25}$, $R^{26}$ and $n_4$ are as defined for formula (I).

Preferably, for the compounds of formula (I), one or two of $R^8$, $R^9$ and $R^{10}$ are the same or different halogen (for example, each halogen is independently selected from the group consisting of F and Cl), and the remaining one or two of $R^8$, $R^9$ and $R^{10}$ are each H.

In another embodiment of the compounds of formula (I), preferably:

$Ar^1$ is

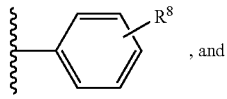, and $Ar^2$ is

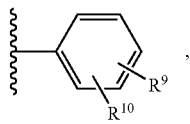, wherein $R^8$ is selected from the group consisting of H and F, and $R^9$ and $R^{10}$ are each independently selected from the group consisting of H, —CH$_3$, F, Cl and —CF$_3$.

In other embodiments of the compounds of formula (I):

$X^1$ is, preferably, selected from the group consisting of —O— and —NR$^{12}$—, and more preferably, $X^1$ is —O—, X is, preferably, selected from the group consisting of —NR$^{20}$—, —O— and —CH$_2$—, when $Ar^1$, $Ar^2$, $R^7$ and/or $R^{11}$ comprise a $(R^{19})_{n7}$ substituent, then preferably $n_7$ is 1 to 3 and each $R^{19}$ substituent is independently selected from the group consisting of H and C$_1$–C$_6$ alkyl (e.g., —CH$_3$); and/or when X is —NR$^{20}$—, then preferably $R^{20}$ is selected from the group consisting of H and C$_1$–C$_6$ alkyl (e.g., —CH$_3$).

In another embodiment of the compounds of formula (I), preferably:

$X^1$ is —O—; and $R^3$, $R^4$, $R^5$, $R^6$, $R^{27}$ and $R^{28}$ are each H.

In another embodiment of the compounds of formula (I), when $R^7$ is selected from the group consisting of H and alkyl, then $R^{11}$ is selected from the group consisting of C$_3$–C$_8$ cycloalkyl, $(R^{16})_{n7}$-aryl-, $(R^{19})_{n7}$-heteroaryl-, —COOR$^{29}$, —CONR$^{21}$R$^{22}$, —CON(R$^{21}$)(CH$_2$)$_n$-G$^1$, —S(O)$_{n5}$(CH$_2$)$_n$-G$^1$, —S(O)$_{n5}$R$^{13}$, —CO(CH$_2$)$_n$-G$^1$ and —(CH$_2$)$_{n1}$-G$^1$.

In another embodiment of the compounds of formula (I), $R^7$ is selected from the group consisting of H and alkyl, and $R^{11}$ is selected from the group consisting of C$_3$–C$_8$ cycloalkyl, $(R^{16})_{n7}$-aryl-, $(R^{19})_{n7}$-heteroaryl-, —COOR$^{29}$, —CONR$^{21}$R$^{22}$, —CON(R$^{21}$)(CH$_2$)$_n$-G$^1$, —S(O)$_{n5}$(CH$_2$)$_n$-G$^1$, —S(O)$_{n5}$R$^{13}$, —CO(CH$_2$)$_n$-G$^1$ and —(CH$_2$)$_{n1}$—G$^1$.

In another embodiment of the compounds of formula (I), $R^7$ is H, and $R^{11}$ is selected from the group consisting of —COOR$^{29}$, —CONR$^{21}$R$^{22}$, —CON(R$^{21}$)(CH$_2$)$_n$-G$^1$, —S(O)$_{n5}$(CH$_2$)$_n$-G$^1$, —S(O)$_{n5}$R$^{13}$, and —CO(CH$_2$)$_n$-G$^1$ wherein said $R^{11}$.

Preferred compounds of formula (I) are the compounds of Examples 48 to 64 (see Table 2 below).

More preferred compounds of the invention include Example Nos. 49, 51, 56, 57 and 64.

The following processes can be used to prepare compounds of the formula (I).

Compounds of formula (I) can be prepared from intermediate compound (5).

Preparation of Intermediate Compound (5)—Methods 1 to 3

Method 1

Step 1

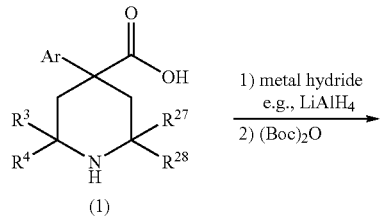

A suitably substituted commercially available piperidine acid (1) can be reduced to the alcohol using metal hydride reducing agents, preferably, LiAlH$_4$. The resulting reaction mixture can be treated with a suitable protective group, such as (Boc)$_2$O, to afford a protected piperidine alcohol (2).

Step 2

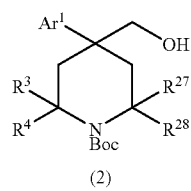

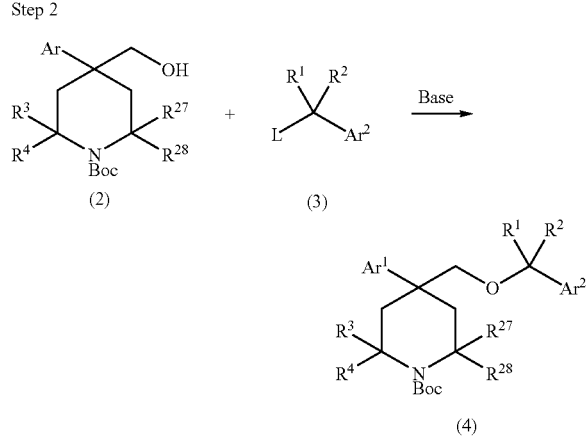

Alkylation of the alcohol (2) is performed by standard conditions, wherein treatment of the alkoxide of (2) with an appropriate halide provides the desired ether. Preferably, R$^1$ and R$^2$ are each H and the leaving group L is bromide or triflate.

Step 3

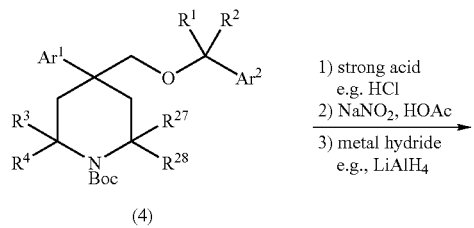

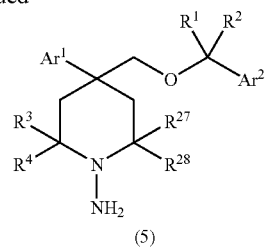

Compound (4) can be deprotected using strong acids, such as HCl (gas or aqueous solution), in neutral, non-reactive solvents, such as ether or dioxane. The resulting piperidine can be treated in biphasic water-methylene chloride mixture containing NaNO$_2$ and HOA-c to give crude nitroso intermediate. The crude nitroso intermediate compound can be reduced with a strong reducing agent, preferably, LiAlH$_4$, to afford the aminopiperidine (5).

Method 2

Step 1

The Boc-protected piperidine (4) can also be made by the following sequence of reactions.

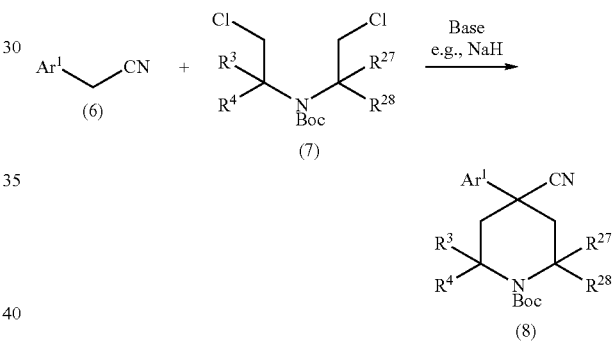

Treatment of the aryl nitrile (6) with an appropriate base, such as NaH, followed by addition of compound (7), provides the substituted piperidine (8). Preferably, a strong base, such as NaH, in a polar aprotic solvent, such as DMSO is used in this reaction.

Step 2

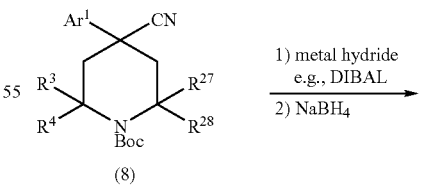

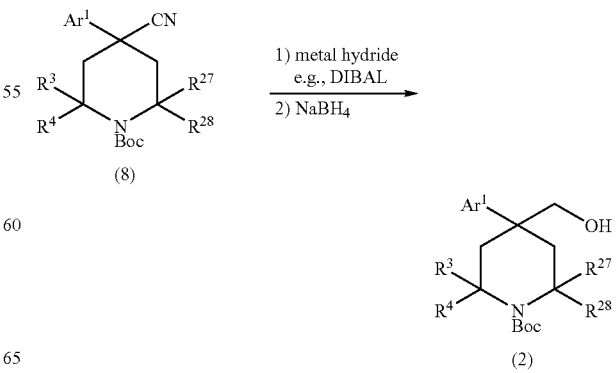

The piperidine nitrile (8) can be converted to the alcohol compound (2) using standard reduction chemistry. The nitrile (8) can be reduced to the corresponding aldehyde using DIBAL. The crude aldehyde can be further reduced to the alcohol (2) using NaBH$_4$.

Alternatively, using techniques well known in the art, the nitrile (8) can be converted to the corresponding acid by hydrolysis with subsequent esterification and reduction to produce alcohol (2).

Following a procedure similar to that in Steps 2 and 3 of Method 1, the alcohol (2) can then be further reacted to produce the aminopiperidine (5).

Method 3

Step 1

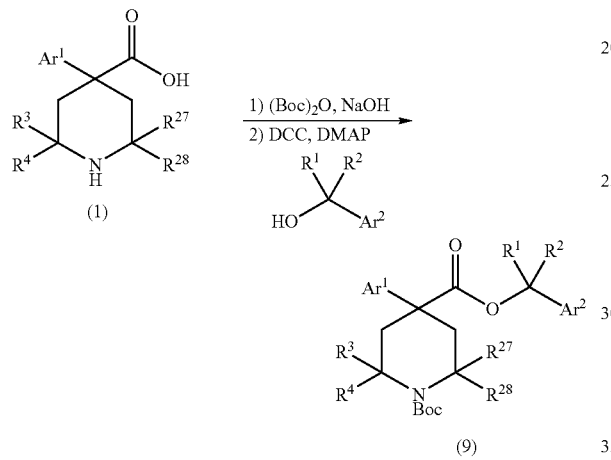

The suitably substituted piperidine acid (1) can be protected using (Boc)$_2$O and NaOH in biphasic conditions, such as water-THF-CH$_2$Cl$_2$. The resulting N-protected acid can then be coupled with a suitably substituted alcohol using carbodiimide, such as DCC, and DMAP to produce compound (9). Preferably, the coupling reaction can be run using 0.25M of starting acid (1) in a 6:1 mixture of toluene and CH$_2$Cl$_2$.

Step 2

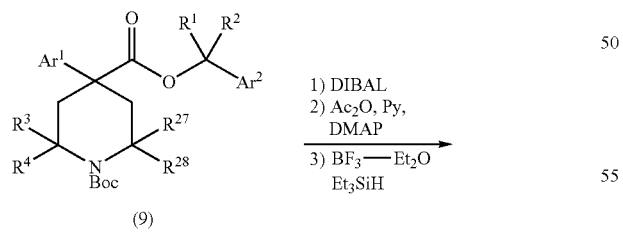

The ester compound (9) can be reduced in two steps using the above reaction. First, the ester (9) can be partially reduced to a hemiacetal that can be trapped with an appropriate anhydride (such as acetic anhydride), pyridine (Py) and dimethylaminopyridine, at a low temperature, such as −78° C. Second, the intermediate acetyl acetal can be further treated with a Lewis acid and a reducing agent (such as a combination of BF$_3$ etherate and triethylsilane), at a low temperature (e.g., −78° C. to 0° C.) to give the Boc protected piperidine (4). Following a procedure similar to that of Step 3 in Method 1, Compound (4) can be reacted to produce the aminopiperidine (5).

Preparation of Compounds of Formula (I) from Compound (5)—Methods 4 to 6

Method 4

Step 1

A suitably substituted aminopiperidine (5) or its corresponding HCl salt can be treated with the corresponding activated carbonyl derivatives of the R$^{11}$ groups in (10) (such as the corresponding acid halides, acid anhydrides and isocyanates), in the presence of a base, such as DIEA.

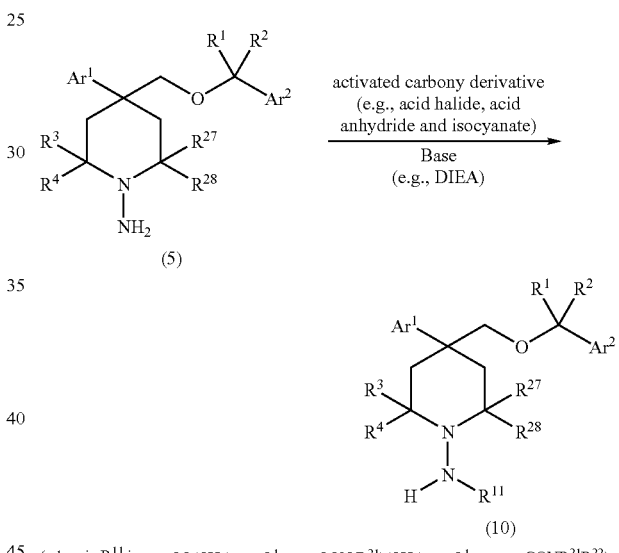

(wherein R$^{11}$ is —CO(CH$_2$)$_n$—G$^1$, —CON(R$^{21}$)(CH$_2$)$_n$—G$^1$ or —CONR$^{21}$R$^{22}$).

Step 2

The acylated aminopiperidine (10) can be treated with a strong base, such as NaH, and an alkylating agent, such as alkyl bromide, or, preferably, alkyl iodide, to give compounds of formula (I) having the formula (I.1). The reaction can be conducted in a polar, aprotic solvent, such as DMF.

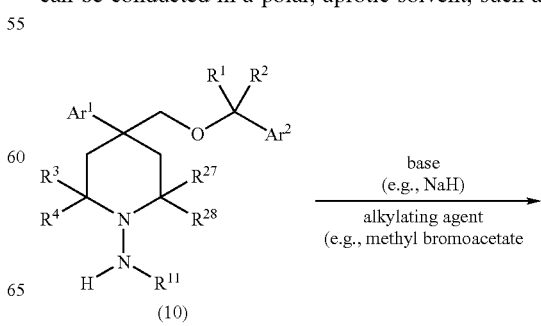

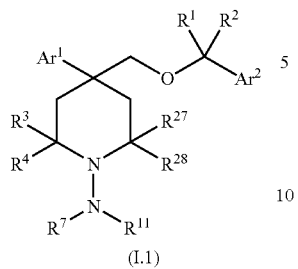

(I.1)

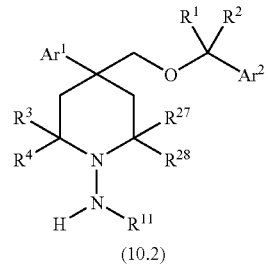

(10.2)

(wherein R[11] is —SO$_2$(CH$_2$)$_n$—G[1]).

Method 5

The aminopiperidine (5) can be treated with a suitably substituted carboxylic acid to afford the aminoamide (10.1). The reaction can be run in CH$_2$Cl$_2$ in the presence of a coupling reagent, such as EDC and HOBt.

Step 2

In the case where n is 0 and G' is —CH=CH$_2$, the vinyl sulfonamide (12) can be further treated with an amine to form compound (13).

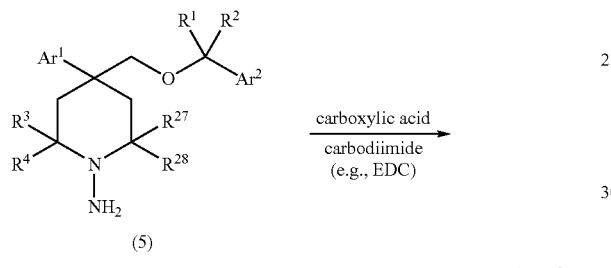

(5)

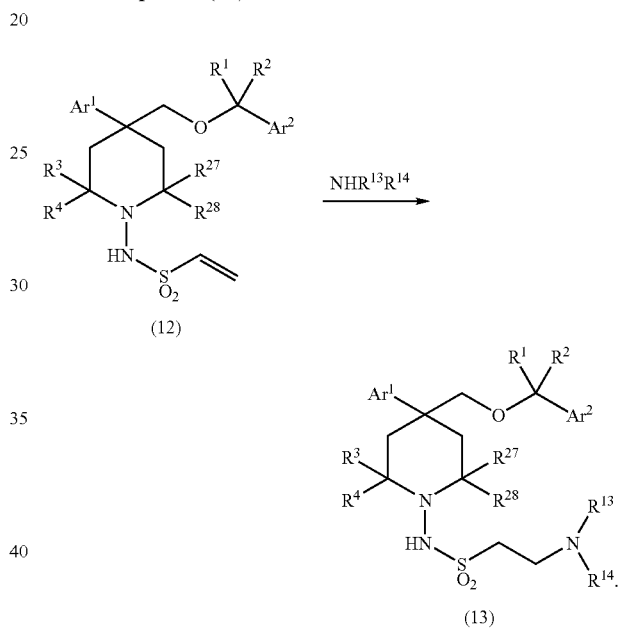

(10.1)

(wherein R[11] is —CO(CH$_2$)$_n$—G[1]).

Preparation of Compounds of the Formula (I.2)—Methods 7 to 11

Compounds of formula (I) having the formula (I.2)

Method 6

Step 1

A suitably substituted aminopiperidine (5) or its corresponding HCl salt can be treated with a suitable sulfonyl chloride (e.g., ClSO$_2$(CH$_2$)$_n$-G[1]) in the presence of a base, (such as DIEA), to give the desired aminosulphonamides (10.2).

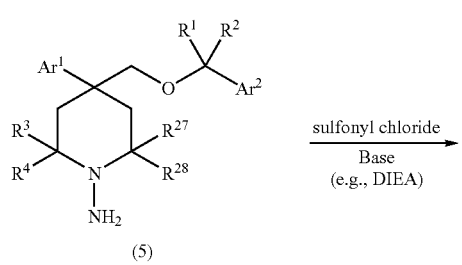

(5)

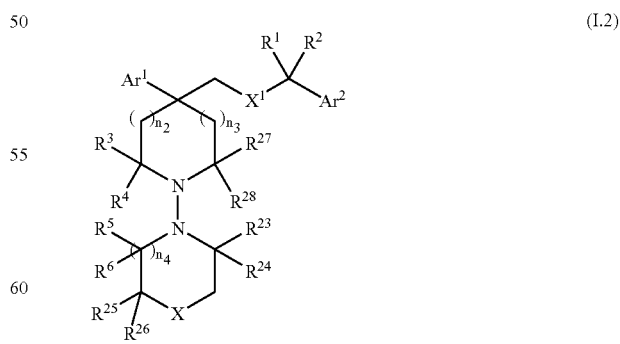

(I.2)

can be prepared in Methods 7 to 11. Compounds of formula (I.2) represent compounds of formula (I) wherein R[7] and R[11] taken together with the nitrogen to which they are bound form the heterocycloalkyl ring

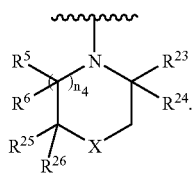

Method 7

Step 1

The aminopiperidine (5) is treated with a suitably substituted acid chloride in the presence of a base, such as DIEA, to give intermediate (14), which has a tethered leaving group (LG). The LG can be a halide, mesylate, tosylate or triflate. Preferably, the LG is iodide, chloride, bromide, mesylate, tosylate or triflate. More preferably, the LG is an iodide group. The reaction can be run in a suitable solvent, such as $CH_2Cl_2$.

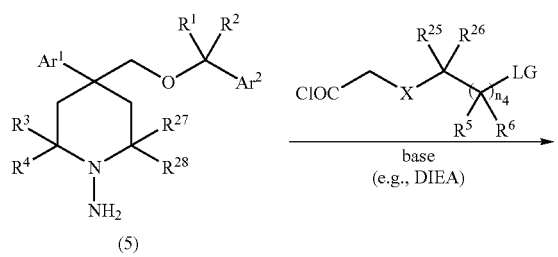

Step 2

The intermediate (14) can be treated with an appropriate base, such as NaH, at ambient temperature to 80° C. in an appropriate solvent, such as THF, to provide compounds of formula (I.2a).

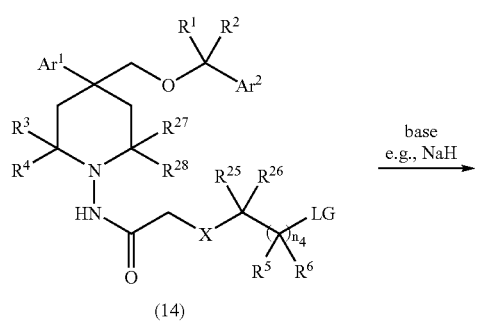

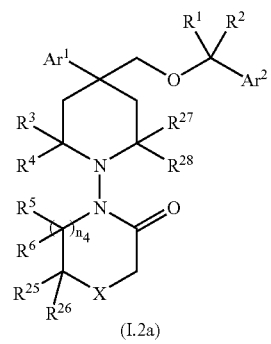

(I.2a)

Method 8

Step 1

Alternatively, the aminopiperidine (5) can be treated with a suitably substituted aldehyde or ketone with a tethered carbonyl ester to effect a reductive amination procedure. The reducing reagent can be $NaBH_4$, $NaBH_3CN$ or, preferably, $NaBH(OAc)_3$. The reaction can be run in $CH_2Cl_2$ or, preferably, $ClCH_2CH_2Cl$.

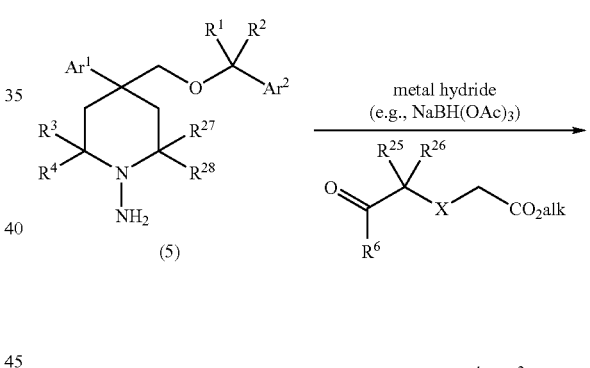

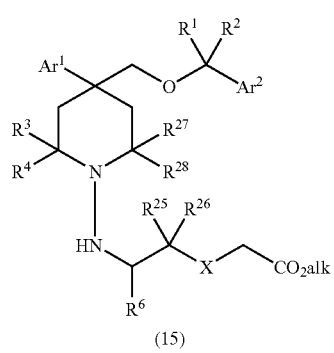

(15)

Step 2

The crude product of step 1 can be treated with a Lewis acid, such as $AlMe_3$, in a high boiling inert solvent, such as toluene, at a temperature ranging from about 80–125° C., to effect the ring closure.

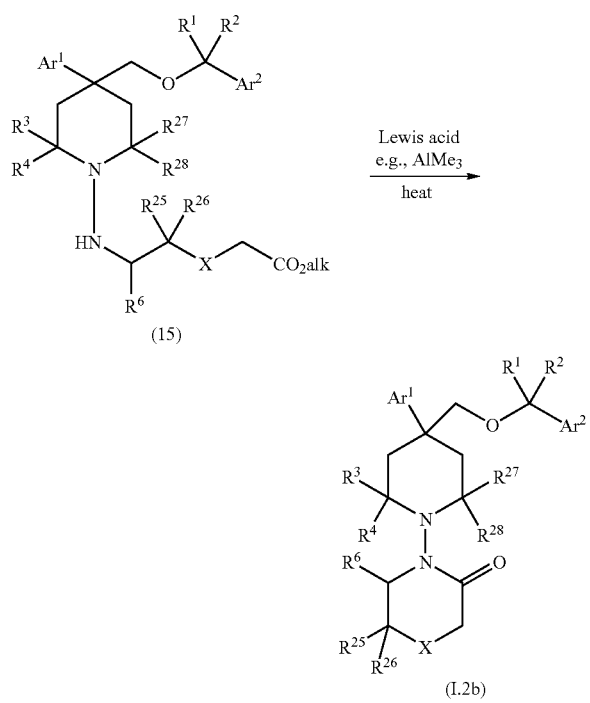

Method 9

The aminopiperidine (5) can be treated with suitably substituted alkyl, preferably, ethyl, esters tethered with a leaving group (LG) at an elevated temperature using $AlMe_3$ to complete the ring closure. The LG can be a halide, preferably, iodide, chloride or bromide, more preferably, an iodide group. The reaction can be run in toluene at a temperature of from ambient to 125° C.

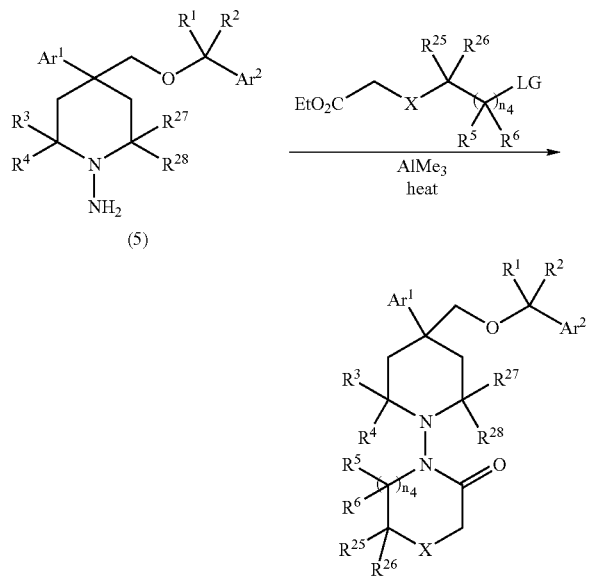

Method 10

Step 1

A suitably substituted aminoalcohol (16) can be treated with p-nitrophenyl-chloroformate in the presence of a base, such as $NaHCO_3$, in THF-water biphasic conditions to afford the protected aminoalcohol (17).

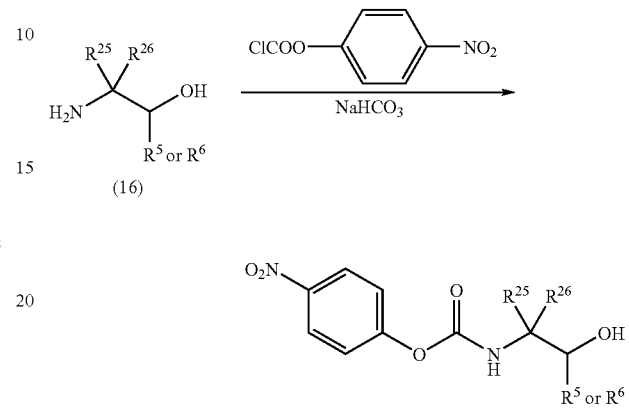

Step 2

The product (17) from Step 2 can be oxidized to the corresponding aldehyde using bleach and a catalytic amount of TEMPO. The reaction can be run in $NaHCO_3$/water biphasic conditions in the presence of NaBr.

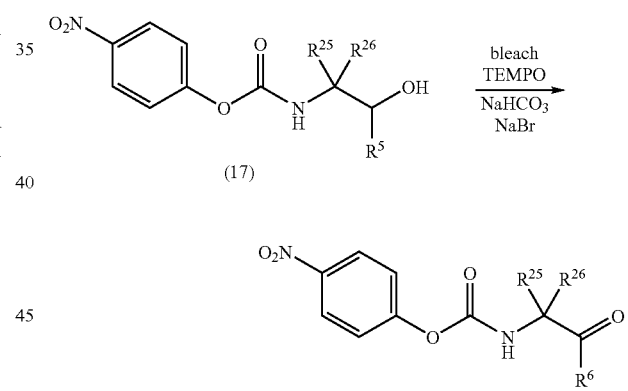

Step 3

The product (18) from Step 2 is treated with aminopiperidine (5) and a metal hydride, such as $NaBH_3CN$, at ambient temperature in an inert solvent, such as THF, followed by heating until the reaction is complete.

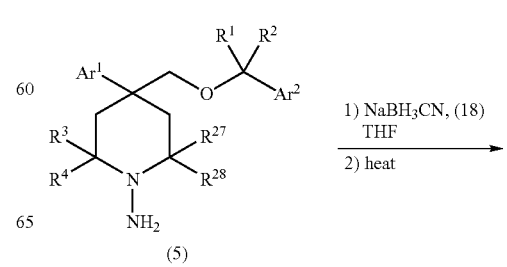

-continued

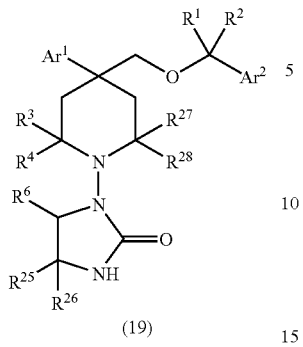

(19)

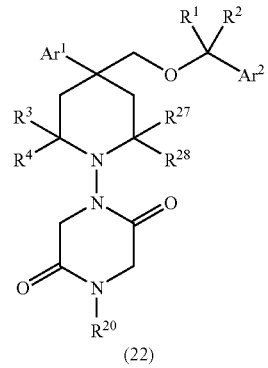

(22)

Method 11

Step 1

A suitably substituted compound from Method 5 bearing a protected amino group, such as Cbz, benzyl or, preferably, Boc, is deprotected using conventional methods.

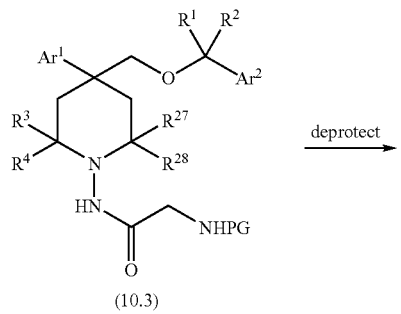

(10.3)

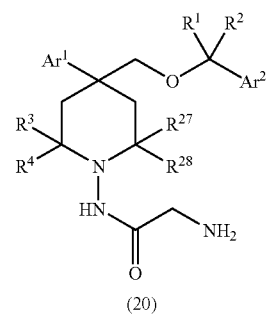

(20)

Step 2

Compound (20) from Step 1 can be treated with a suitably substituted haloacetyl halide, and subsequent cyclization provides the desired diketopiperazine. One skilled in the art will recognize that alternative methods for the synthesis of diketopiperazines can be employed to provide this class of compounds.

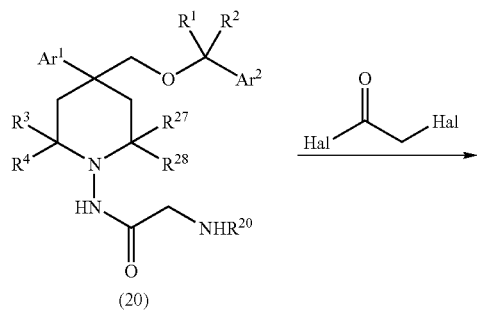

(20)

Assay

The in vitro and in vivo $NK_1$, $NK_2$ and $NK_3$ activities of the compounds having the formula (I) can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \ MSB = \frac{(\text{dpm of unknown}) - (\text{dpm of nonspecific binding})}{(\text{dpm of total binding}) - (\text{dpm of nonspecific binding})} \times 100$$

The concentration at which the compound produces 50% inhibition of binding is then used to determine an inhibition constant ("Ki") using the Chang-Prusoff equation. In vivo activity may be measured by inhibition of an agonist-induced foot tapping in a gerbil, as described in Science, 281, 1640–1695 (1998), which is herein incorporated by reference thereto.

The final compounds of Examples 1 to 64 had a $K_i$ in the range of about 100 nM to about 0.3 nM.

The final compounds of Examples 48 to 64 had a $K_i$ in the range of about 11 nM to about 0.3 nM.

The final compounds of Examples 49, 51, 56, 57 and 64 had a $K_i$ in the range of about 3 to about 0.3 nM.

The final compound of Example 56 had a $K_i$ of about 0.3 nM.

Compounds of formula (I) are effective antagonists of the $NK_1$ receptor, and have an effect on its endogenous agonist, Substance P, at the $NK_1$ receptor site, and therefore, can be useful in treating conditions caused or aggravated by the activity of said receptor.

Compounds of the formula (I) have a number of utilities. For instance, the inventive compounds can be useful as antagonists of neurokinin receptors, particularly, $NK_1$ receptors in a mammal, such as a human. As such, they may be useful in treating and preventing one or more of a variety of mammalian (human and animal) disease states (physiological disorders, symptoms and diseases) in a patient in need of such treatment, wherein said disease states are selected from the group consisting of: (1) respiratory diseases (e.g., chronic lung disease, bronchitis, pneumonia, asthma, allergy, cough and bronchospasm), (2) inflammatory diseases (e.g., arthritis and psoriasis), (3) skin disorders (e.g., atopic dermatitis and contact dermatitis), (4) ophthalmological disorders (e.g., retinitis, ocular hypertension and cataracts), (5) central nervous system conditions, such as depressions (e.g., neurotic depression), anxieties (e.g., general anxiety, social anxiety and panic anxiety disorders), phobias (e.g., social phobia), and bipolar disorder, (6) addictions (e.g., alcohol dependence and psychoactive substance abuse), (7) epilepsy, (8) nociception, (9) psychosis, (10) schizophrenia, (11) Alzheimer's disease, (12) AIDs related dementia, (13) Towne's disease, (14) stress related disorders (e.g., post tramautic stress disorder), (15) obsessive/compulsive disorders, (16) eating disorders (e.g., bulemia, anorexia nervosa and binge eating), (17) sleep disorders, (18) mania, (19) premenstrual syndrome, (20) gastrointestinal disorders (e.g., irritable bowel syndrome, Crohn's disease, colitis, and emesis), (21) atherosclerosis, (22) fibrosing disorders (e.g., pulmonary fibrosis), (23) obesity, (24) Type II diabetes, (25) pain related disorders (e.g., headaches, such as migraines, ryeuropathic pain, post-operative pain, and chronic pain syndromes), (26) bladder and genitourinary disorders (e.g., interstitial cystitis and urinary incontinence), and (27) nausea.

Preferably, the inventive compounds can be useful in treating and preventing one of the following mammalian (e.g., human) disease states in a patient in need of such treatment: respiratory diseases (e.g., cough), depression, anxiety, phobia, and bipolar disorder, alcohol dependence, psychoactive substance abuse, nociception, psychosis, schizophrenia, stress related disorders, obsessive/compulsive disorder, bulemia, anorexia nervosa and binge eating, sleep disorders, mania, premenstrual syndrome, gastrointestinal disorders, obesity, pain related disorders, bladder disorders, genitourinary disorders, emesis and nausea. In particular, the compounds having the formulas (I) are useful for treating disease states related to microvascular leakage and mucus secretion. Consequently, the compounds of the invention are especially useful in the treatment and prevention of asthma, emesis, nausea, depressions, anxieties, cough and pain related disorders, more especially, emesis, depression, anxiety and cough.

In another aspect, the invention relates to pharmaceutical compositions comprising at least one compound (e.g., one to three compounds, preferably, one compound) represented by the formula (I) and at least one pharmaceutically-acceptable excipient or carrier. The invention also relates to the use of such pharmaceutical compositions in the treatment of mammalian (e.g., human) disease states, such as those listed above.

In still another aspect of the invention, a method is provided for antagonizing an effect of a Substance P at a neurokinin-1 receptor site or for the blockade of one or more neurokinin-1 receptors in a mammal (i.e., a patient, e.g., a human) in need of such treatment, comprising administering to the mammal an effective amount of at least one (e.g., one) compound having the formula (I).

In another embodiment of the invention, an effective amount of one or more of the inventive $NK_1$ receptor antagonists may be combined with an effective amount of one or more anti-depressant agents and/or one or more anti-anxiety agents (e.g., gepirone (e.g., gepirone hydrochloride), and nefazodone (e.g., nefazodone hydrochloride, e.g., Serzone®) to treat depression and/or anxiety. U.S. Pat. No. 6,117,855 (2000), the disclosure of which is incorporated herein by reference thereto, discloses a method for treating or preventing depression or anxiety with a combination therapy of a specific $NK_1$ receptor antagonist together with an anti-depressant and/or anti-anxiety agent. Thus, antidepressant and/or anti-anxiety agents, such as those disclosed in U.S. Pat. No. 6,117,855 (2000), can be combined with one or more (e.g., one) compounds of the formula (I) to treat depression and/or anxiety disease states in a mammal, preferably, a human.

In still another embodiment of the invention, an effective amount of one or more (e.g., one) of the inventive $NK_1$ receptor antagonists may be combined with an effective amount of one or more (e.g., one) selective serotonin reuptake inhibitors ("SSRIs") to treat a variety of mammalian disease states, such as those described above. SSRIs alter the synaptic availability of serotonin through their inhibition of presynaptic reaccumulation of neuronally released serotonin. U.S. Pat. No. 6,162,805 (2000), the disclosure of which is incorporated herein by reference thereto, discloses a method for treating obesity with a combination therapy of a $NK_1$ receptor antagonist and an SSRI. An inventive compound(s) of the formula (I) can be combined together with an SSRI(s) in a single pharmaceutical composition, or it can be administered simultaneously, concurrently or sequentially with an SSRI. This combination may be useful in the treatment and prevention of obesity or another of the above-identified human and animal disease states. In particular, an effective amount of at least one (e.g., one) compound having the formula (I), alone or together with an effective amount of at least one (e.g., one) selective serotonin reuptake inhibitor, can be useful in the treatment and prevention of depression, and/or anxiety.

Numerous chemical substances are known to alter the synaptic availability of serotonin through their inhibition of presynaptic reaccumulation of neuronally released serotonin. Representative SSRIs include, without limitation, the following: fluoxetine (e.g., fluoxetine hydrochloride, e.g., Prozac®), fluvoxamine (e.g., fluvoxamine maleate, e.g. Luvox®), paroxetine (e.g., paroxetine hydrochloride, e.g., Paxil®), sertraline (e.g., sertraline hydrochloride, e.g., Zoloft®), citalopram (e.g., citalopram hydrobromide, e.g., Celexa™), duloxetine (e.g., duloxetine hydrochloride), and venlafaxine (e.g., venlafaxine hydrochloride, e.g., Effexor®). Further SSRIs include those disclosed in U.S. Pat. No. 6,162,805 (2000). Other compounds can readily be evaluated to determine their ability to selectively inhibit serotonin reuptake. Thus, one aspect of the invention relates to a pharmaceutical composition comprising at least one (e.g., one) $NK_1$ receptor antagonist having the formula (I), at least one (e.g., one) SSRI, and at least one pharmaceutically-acceptable excipient or carrier. Another aspect of the invention relates to a method of treating the above identified mammalian (e.g., human) disease states, the method comprising administering to a patient in need of such treatment an effective amount of a pharmaceutical composition comprising at least one (e.g., one) $NK_1$ receptor antagonist having the formula (I) in combination with at least one (e.g., one) SSRI, such as one of those recited above, and at least one pharmaceutically-acceptable excipient or carrier.

In a preferred aspect, the invention relates to a method of treating depression and anxiety, the method comprising administering to a patient in need of such treatment an effective amount of at least one (e.g., one) $NK_1$ receptor antagonist having the formula (I) in combination with at least one (e.g., one) SSRI, such as one of those described above. When an inventive $NK_1$ receptor antagonist is combined with an SSRI for administration to a patient in need of such treatment, the two active ingredients can be administered simultaneously, consecutively (one after the other within a relatively short period of time), or sequentially (first one and then the other over a period of time). In general, when the two active ingredients are administered consecutively or sequentially, the inventive $NK_1$ receptor antagonist is, preferably, administered before the administration of the SSRI.

It is another embodiment of the invention to treat a patient suffering from multiple ailments with a combination therapy, said therapy comprising administering to a patient (e.g., a mammal, preferably a human) in need of such treatment at least one compound of formula (I), and at least one other active ingredient (i.e., drug) used for treating one-or more of the ailments being suffered by said patient. The compounds of formula (I) and the other active ingredients can be administered sequentially, concurrently and/or simultaneously. The compounds of formula (I) and the other active ingredients can be administered separately in any suitable dosage form. Preferably, administration is accomplished using an oral dosage forms or using a transdermal patches. The compounds of formula (I) and the other active ingredients can be formulated together and administered in one combined dosage form.

Thus, the compounds of the invention may be employed alone or in combination with other active agents. Combination therapy includes the administration of two or more active ingredients to a patient in need of treatment. In addition to the above described $NK_1$ receptor antagonist/SSRI combination therapy, the compounds having the formula (I) may be combined with one or more other active agents, such as the following: other types of $NK_1$ receptor antagonists (e.g., those that are disclosed in the neurokinin receptor antagonist patents cited above in the Background of the Invention section), prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists (e.g., ondansetron (e.g., ondansetron hydrochloride, e.g., Zolfran®), palonosetron and granisetron (e.g., granisetron hydrochloride, e.g., Kytril®)), serotonin 5-$HT_2$ receptor agonists, nociceptin receptor agonists, glucocorticoids (e.g., dexamethasone), rho kinase inhibitors, potassium channel modulators and/or inhibitors of multi-drug resistance protein 5.

Preferable therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; ETA antagonists, such as bosentan and ABT-627; serotonin 5-$HT_3$ receptor antagonists, such as ondansetron; and glucocorticoids, such as dexamethasone. In preferred embodiments of the invention, the inventive compounds can be combined with: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and/or inhibitors of multi-drug resistance protein 5.

A preferred embodiment of the invention is directed to a method of treating emesis and/or nausea in a patient in need of such treatment using a combination therapy comprising administering to said patient an effective amount of at least one (e.g., one) compound having the formula (I) in combination with an effective amount of at least one (e.g., one) serotonin 5-$HT_3$ receptor antagonist (e.g., ondansetron) and/or at least one (e.g., one) glucocorticoid (e.g., dexamethasone). Preferably, the compound of formula (I) is administered orally or by IV.

Another embodiment of this invention is directed to a method for treating a physiological disorder, symptom or disease in a patient in need of such treatment, comprising administering to said patient an effective amount of at least one compound of formula 1, and an effective amount of at least one active ingredient selected from the group consisting of: other $NK_1$ receptor antagonists, selective serotonin reuptake inhibitors, dopamine receptor agonists, serotonin 5-$HT_3$ receptor antagonists, serotonin 5-$HT_{2c}$ receptor agonists, nociceptin receptor agonists, glucocorticoids and inhibitors of multidrug resistance protein 5, wherein said physiological disorder, symptom or disease is selected from the group consisting of: a respiratory disease, depression, anxiety, phobia, bipolar disorder, alcohol dependence, psychoactive substance abuse, nociception, psychosis, schizophrenia, stress related disorder, obsessive/compulsive disorder, bulimia, anorexia nervosa, binge eating, sleep disorder, mania, premenstrual syndrome, gastrointestinal disorder, obesity, headache, neuropathic pain, post-operative pain, chronic pain syndrome, bladder disorder, genitourinary disorder, cough, emesis and nausea.

Another aspect of the invention is to provide a kit comprising, in separate containers in a single package, pharmaceutical compositions for use in combination to treat an $NK_1$ receptor mediated disease, wherein one container comprises a pharmaceutical composition comprising an effective amount of a compound of formula (I) in a pharmaceutically acceptable carrier, and wherein, a separate container comprises a pharmaceutical composition comprising another therapeutic agent in a pharmaceutically acceptable carrier, said therapeutic agent being selected from the group consisting of: SSRIs, other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin 5-$HT_3$ receptor antagonists, serotonin 5-$HT_{2c}$ receptor agonists, nociceptin receptor agonists, glucocorticoids, rho kinase inhibitors, potassium channel modulators and inhibitors of multi-drug resistance protein 5.

Another aspect of the invention is to provide a kit comprising, in separate containers in a single package, pharmaceutical compositions for use in combination to treat depression and/or anxiety, wherein one container comprises a pharmaceutical composition comprising an effective amount of a compound of formula (I) in a pharmaceutically acceptable carrier, and wherein, a separate container comprises a pharmaceutical composition comprising an antidepressant agent in a pharmaceutically acceptable carrier, and/or wherein a separate container comprises a pharmaceutical composition comprising an antianxiety agent in a pharmaceutically acceptable carrier.

Another aspect of the invention is to provide a kit comprising, in separate containers in a single package, pharmaceutical compositions for use in combination to treat an $NK_1$ receptor mediated disease, wherein one container comprises a pharmaceutical composition comprising an effective amount of a compound of formula (I) in a pharmaceutically acceptable carrier, and wherein, a separate container comprises a pharmaceutical composition comprising an SSRI in a pharmaceutically acceptable carrier.

Another aspect of the invention is to provide a kit comprising, in separate containers in a single package, pharmaceutical compositions for use in combination to treat depression and/or anxiety, wherein one container comprises a pharmaceutical composition comprising an effective amount of a compound of formula (I) in a pharmaceutically acceptable carrier, and wherein, a separate container comprises a pharmaceutical composition comprising an SSRI in a pharmaceutically acceptable carrier.

Another aspect of the invention is to provide a kit comprising, in separate containers in a single package, pharmaceutical compositions for use in combination to treat emesis and/or nausea, wherein one container comprises a pharmaceutical composition comprising an effective amount of a compound of formula (I) in a pharmaceutically acceptable carrier, and wherein, a separate container comprises a pharmaceutical composition comprising a serotonin 5-$HT_3$ receptor antagonist in a pharmaceutically acceptable carrier, and/or wherein a separate container comprises a pharmaceutical composition comprising a glucocorticoid in a pharmaceutically acceptable carrier.

Another aspect of the invention is to provide a kit comprising, in separate containers in a single package, pharmaceutical compositions for use in combination to treat emesis and/or nausea, wherein one container comprises a pharmaceutical composition comprising an effective amount of a compound of formula (I) in a pharmaceutically acceptable carrier, and wherein, a separate container comprises ondansetron, and/or wherein a separate container comprises dexamethasone.

Another aspect of the invention is to provide a kit comprising, in separate containers in a single package, pharmaceutical compositions for use in combination to treat an $NK_1$ receptor mediated disease, wherein one container comprises a pharmaceutical composition comprising an effective amount of a compound of formula (I) in a pharmaceutically acceptable carrier, and wherein, a separate container comprises a pharmaceutical composition comprising a therapeutic agent in a pharmaceutically acceptable carrier, said therapeutic agent being selected from the group consisting of: other types of $NK_1$ receptor antagonists, SSRIs, dopamine receptor agonists, serotonin 5-$HT_3$ receptor antagonists, serotonin 5-$HT_{2c}$ receptor agonists, nociceptin receptor agonists, glucocorticoids and inhibitors of multi-drug resistance protein 5.

Pharmaceutical compositions may contain from about 0.1 to about 99.9 weight percent, or from about 5 to about 95 weight percent, or from about 20 to about 80 weight percent of active ingredient (compound of the formula (I)).

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4000 mg, preferably from about 0.02 mg to about 1000 mg, more preferably from about 0.3 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The pharmaceutical compositions of the invention may be administered from about 1 to about 5 times per day, or alternatively, as a continuous infusion. Such administration can be used as a chronic or acute therapy.

The quantity of $NK_1$ receptor antagonist in combination with a selective serotonin reuptake inhibitor ("SSRI") in a unit dose of preparation may be from about 10 to about 300 mg of $NK_1$ receptor antagonist combined with from about 10 to about 100 mg of SSRI. In another combination the quantity of $NK_1$ receptor antagonist in combination with a SSRI in a unit dose of preparation may be from about 50 to about 300 mg of $NK_1$ receptor antagonist combined with from about 10 to about 100 mg of SSRI. In another combination the quantity of $NK_1$ receptor antagonist in combination with SSRI in a unit dose of preparation may be from about 50 to about 300 mg of NK, receptor antagonist combined with from about 20 to about 50 mg of SSRI.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Specific dosage and treatment regimens for any particular patient may be varied and will depend upon a variety of factors, including the activity of the specific compound employed, the age, body weight, general health status, sex and diet of the patient, the time of administration, the rate of excretion, the specific drug combination, the severity and course of the symptoms being treated, the patient's disposition to the condition being treated and the judgment of the treating physician. Determination of the proper dosage regimen for a particular situation is within the skill of the art.

EXAMPLES

The following examples are intended to illustrate, but not to limit, the scope of the invention.

Example Nos. 1–47

Compounds of the formula

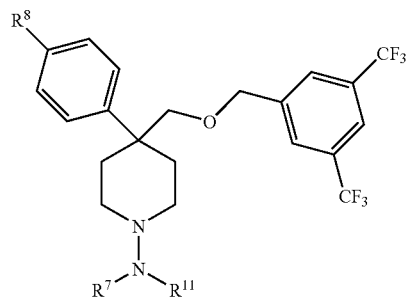

wherein $R^7$, $R^8$ and $R^{11}$ are described in Table 1 are prepared by the procedures described after Table 1.

TABLE 1

| Example Nos. | $R^8$ | $R^7$ | $R^{11}$ | LRMS (m + H) |
|---|---|---|---|---|
| 1 | H | H | H | 433.4 |
| 2 | H | H | | 475.5 |
| 3 | H | H | | 503.5 |
| 4 | H | H | | 529.4 |
| 5 | H | H | | 519.5 |
| 6 | H | H | | 533.5 |

TABLE 1-continued
| Example Nos. | R⁸ | R⁷ | R¹¹ | LRMS (m + H) |
|---|---|---|---|---|
| 7 | H | H | 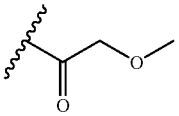 | 505.5 |
| 8 | H | H | 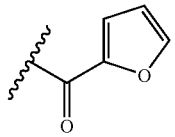 | 527.5 |
| 9 | H | H | 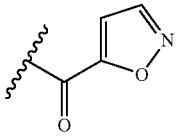 | 528.5 |
| 10 | H | H | 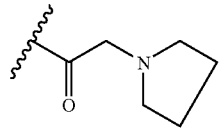 | 544.5 |
| 11 | H | H | 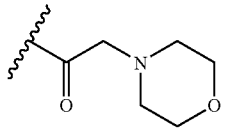 | 560.5 |
| 12 | H | H | 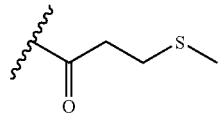 | 535.6 |
| 13 | H | H | 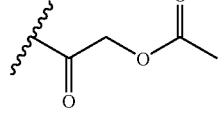 | 533.5 |
| 14 | H | H | 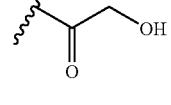 | 491.4 |
| 15 | H | H | 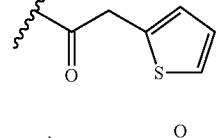 | 557.6 |
| 16 | H | H | 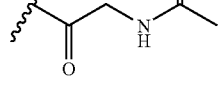 | 532.5 |

TABLE 1-continued
| Example Nos. | R⁸ | R⁷ | R¹¹ | LRMS (m + H) |
|---|---|---|---|---|
| 17 | H | H | 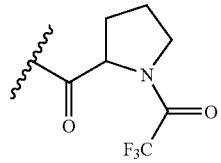 | 626.5 |
| 18 | H | H | 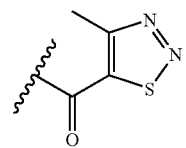 | 559.5 |
| 19 | H | H | 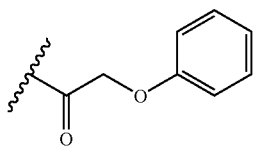 | 567.5 |
| 20 | H | H | 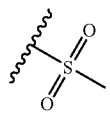 | 511.4 |
| 21 | H | H | 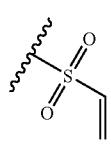 | 523.5 |
| 22 | H | H | 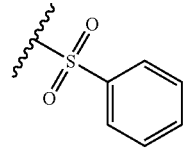 | 573.5 |
| 23 | H | H | 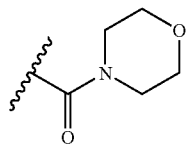 | 546.5 |
| 24 | H | H | 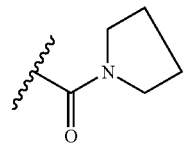 | 530.5 |
| 25 | H | H | 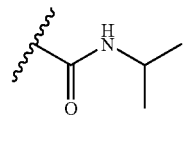 | 518.5 |
| 26 | H | H | 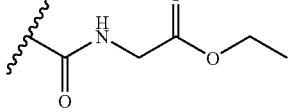 | 562.5 |

TABLE 1-continued

| Example Nos. | R⁸ | R⁷ | R¹¹ | LRMS (m + H) |
|---|---|---|---|---|
| 27 | H | H | -C(O)NH-allyl | 516.5 |
| 28 | H | H | -C(O)NH₂ | 476.4 |
| 29 | H | methyl propanoate | isoxazol-5-yl carbonyl | 600.5 |
| 30 | H | 2-methylthiazol-4-ylmethyl | isoxazol-5-yl carbonyl | 639.6 |
| 31 | F | H | tert-butyl ester | 551.5 |
| 32 | F | H | H | 451.4 |
| 33 | F | H | trifluoromethyl ketone | 547.4 |
| 34 | F | H | methyl 2-oxoacetate | 537.4 |
| 35 | F | H | methyl 3-oxobutanoate | 551.5 |
| 36 | F | H | methoxymethyl ketone | 523.5 |
| 37 | F | H | furan-2-yl carbonyl | 545.4 |

TABLE 1-continued
| Example Nos. | R⁸ | R⁷ | R¹¹ | LRMS (m + H) |
|---|---|---|---|---|
| 38 | F | H | 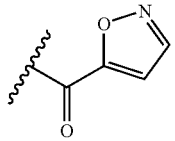 | 546.6 |
| 39 | F | H | 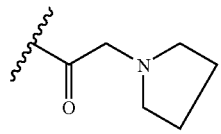 | 548.5 |
| 40 | H | H | 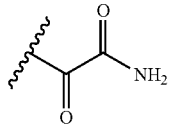 | 504.4 |
| 41 | H | H | 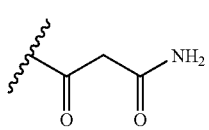 | 518.5 |
| 42 | F | H | 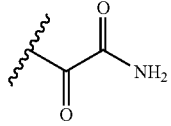 | 522.4 |
| 43 | F | H | 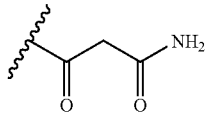 | 536.5 |
| 44 | H | H | 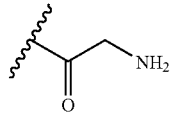 | 490.4 |
| 45 | H | H | 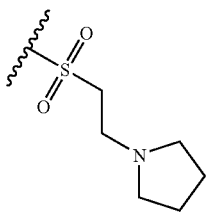 | 594.6 |
| 46 | H | H | 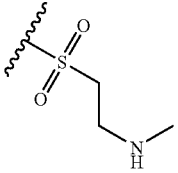 | 554.6 |

TABLE 1-continued

| Example Nos. | $R^8$ | $R^7$ | $R^{11}$ | LRMS (m + H) |
|---|---|---|---|---|
| 47 | H | H | 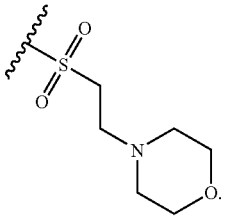 | 610.6 |

Example 1

Method 1

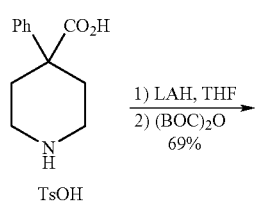

TsOH

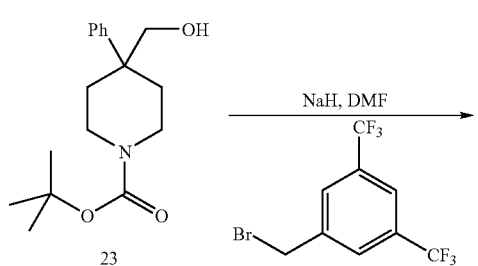

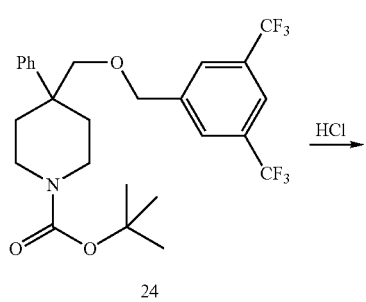

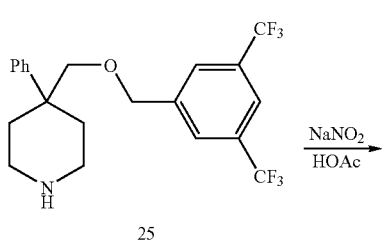

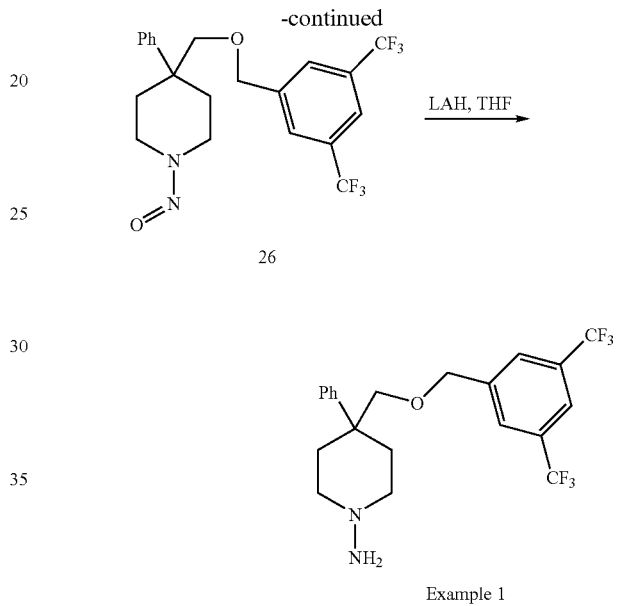

Example 1

Step 1

At 0° C., to a mixture of commercially available 4-phenyl-4-carboxy piperidine tosylate (20 g, 52.9 mmol) in 100 mL of anhydrous THF, was added dropwise 106 mL of 1.0 M of LAH solution in THF. After the addition, the resultant suspension was refluxed for 90 min, and allowed to cool to room temperature, then quenched by addition of 6.4 mL of 2 N NaOH aqueous solution and 8 mL of water. Another solution of 2.1 g of NaOH in 25 mL of water was added, followed by addition of a solution of di-tert-butyl-dicarbonate (11.56 g, 52.9 mmol, 1 equiv.) in 65 mL of dichloromethane. The mixture was stirred at room temperature for 18 hours, then filtered through a sodium sulfate pad. The filtrate was dried under vacuum, and then taken up with dichloromethane. The organic solution was washed with 10% NaOH (100 mL), water (100 mL), and brine (100 mL), then dried over anhydrous $MgSO_4$, filtered and concentrated to give an oil as the crude product, which upon recrystallization in ethyl ether, provided the Boc-amino alcohol 23 as a white solid (10.5 gram, yield 69%). MS:292 (M+1).

Step 2

To a solution of the carbinol 23 (3.34 g, 11.5 mmol, 1 equiv.) and 3,5-bis(trifluoromethyl)benzyl bromide (2.1 mL, 11.5 mmol, 1 equiv.) in 20 mL of dry DMF, was added slowly 60% NaH dispersion in mineral oil (0.59 g, 14.8 mmol, 1.29 equiv.). After stirring at room temperature overnight, the reaction mixture was poured into 500 mL of water, then extracted with 230 mL of EtOAc. The organic layer was washed with water (3×230 mL) and brine, and then dried over $Na_2SO_4$, filtered and concentrated. Flash chromatography eluting with Hexane/EtOAc 95/5→90/10 gave 4.66 g of 24 (yield 78%).

Step 3

A solution of 1-tert-Butoxycarbonyl-4-phenyl-4[(3,5-bis-trifluoromethyl) benzyloxymethyl] piperidine 24 (0.965 g, 1.86 mmol, 1 equiv.) in 30 mL of dry diethyl ether was streamed with hydrogen chloride gas for 40 min. The resultant solution was stirred for another 2.5 hours at room temperature. The solvent was removed to give a solid. The crude product was taken up with dichloromethane and neutralized with 1 N NaOH (about 10 mL). The aqueous layer was further extracted with EtOAc. The combined organic layer was washed with brine, dried over $Na_2SO_4$, and concentrated to give 0.639 g product 25 as the free base.

Step 4

A solution of 25 (470 mg as in free form, 1.13 mmol, 1 equiv.) in 5 mL dry THF was treated with a solution of $NaNO_2$ (160 mg, 2.25 mmol, 2 equiv.) in 5 mL of water. After cooling to 0° C., the mixture was treated with 0.09 mL of acetic acid. After stirring overnight, the mixture was neutralized with an excess of $Na_2CO_3$. The mixture was filtered through a sintered glass funnel, and concentrated. The aqueous layer was extracted with EtOAc (2×50 mL). The organic layer was dried over $Na_2SO_4$, and then concentrated to give 450 mg of the product 26 (90%).

Step 5

A solution of nitroso compound 26 (20.18 g, 45.2 mmol, 1 equiv.) in 250 mL of dry $Et_2O$ was treated with 81 mL of 1.0 M LAH in $Et_2O$ at −2° C. for a period of 30 min. After TLC showed the reaction was nearly complete, it was quenched by adding 100 mL of EtOAc, and then 60 mL of ice-cold water. The mixture was filtered through a sintered glass funnel, and the residue was washed with $Et_2O$ (3×100 mL). The combined organic layer was dried over $Na_2SO_4$, and concentrated to give 14.5 g of the product (yield 74%). It was found that the amino-piperidine is more stable as its hydrogen chloride salt, which can be obtained by treating the product in free base form with 1 equivalent of hydrogen chloride solution in $Et_2O$.

Method 2

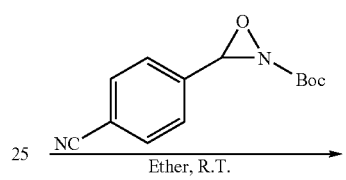

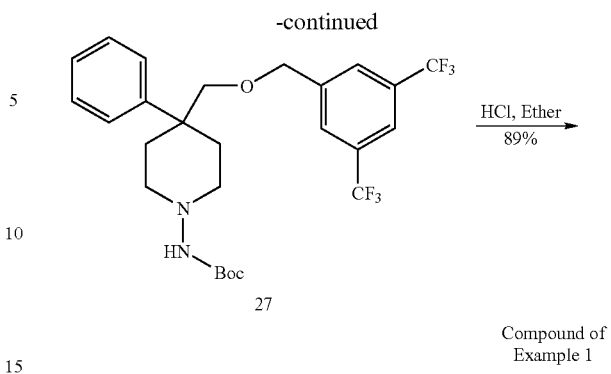

Compound of Example 1

Step 1

4-phenyl-4-[(3,5-bistrifluoromethyl)benzyloxymethyl]piperidine (25)) (417 mg, 1 mmol) was dissolved in $CH_2Cl_2$ (2 mL), and was added dropwise to the solution of 3-(4-cyanophenyl)-1-oxaziridine carboxylate (246 mg, 1 mmol) in ether (3 mL). Stirred at 23° C. for 30 min and concentrated to give the crude product. Separated on flash chromatography using hexane and EtOAc (1:9) to yield the product (411 mg, 77%).

Step 2

Treated the product of Step 1 with HCl in ether using a procedure similar to Step 3 in Method 1 of Example 1 to afford the desired product (about 100%).

Example 2

Dissolved the compound of Example 1 (120 mg, 0.28 mmol) in $CH_2Cl_2$ (3 mL) and treat with acetyl chloride and diisopropylethylamine at 0° C. Stirred for an additional 30 min and concentrated to afford a crude product. Purified the product on column chromatograph using 1:99 MeOH (with $NH_3$) and $CH_2Cl_2$ to give the compound of Example 2 (18 mg, 14%). Alternatively, the compound of Example 1 was reacted with acetic acid using standard EDC/HOBt coupling conditions to afford the desired compound.

Examples 3–19

Employing a procedure similar to that described in Example 2, and using the corresponding acid chloride or carboxylic acid, provided the appropriate amide. For Examples 10 and 11, using a procedure similar to that described in Example 2 but using chloroacetyl chloride in place of acetyl chloride gave the crude α-chloroamide. Treated the α-chloroamide with pyrrolidine or morpholine at room temperature for 24-48 h provided Examples 10 and 11, respectively.

Examples 20–22

Using a procedure similar to that described in Example 2, using the corresponding sulfonyl chloride afforded the appropriate sulfonamide.

Examples 23–28

Using a procedure similar to that described in Example 2, substituting the corresponding isocyanate gave the appropriate urea.

Example 29

Dissolved the compound of Example 9 (310 mg, 0.59 mmol) in anhydrous DMF (2 mL), added sodium hydride (31 mg, 0.77 mmol) at 0° C. and stirred for 30 min. Treated the mixture with bromomethylacetate (68 μL, 0.71 mmol), and stirred for additional 2 hours at 23° C. Removed the solvent, quenched with saturated NaHCO$_3$ solution, and extracted with CH$_2$Cl$_2$ (2×15 mL). The combined organic layer was dried over MgSO$_4$ and concentrated to yield a crude product. Purified on column chromatography using MeOH (sat. with NH$_3$) and CH$_2$Cl$_2$ (1:99) to give the target compound.

Example 30

Using a procedure similar to the one described in Example 29, substituting bromomethylacetate with thiazolemethylbromide afforded the target compound.

Example 31

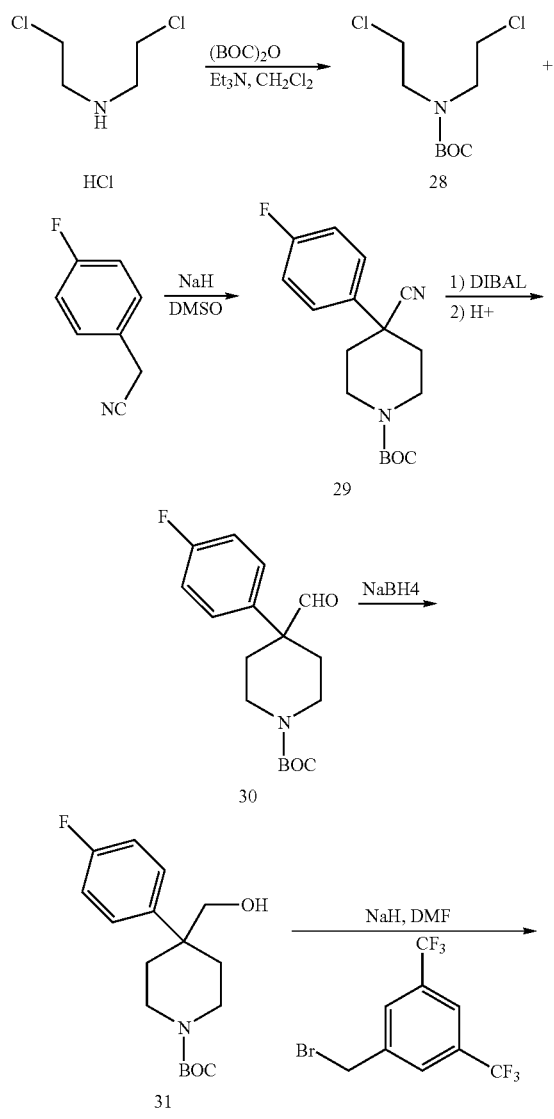

-continued

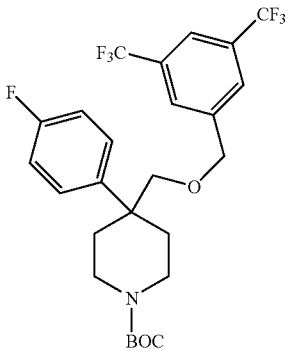

Example 31

Step 1

To a suspension of bis(2-chloroethyl)amine hydrochloride (55 g, 0.31 mol, 1.09 equiv.) and (BOC)$_2$O (62 g, 0.28 mmol, 1 equiv.) in 380 mL CH$_2$Cl$_2$, was added dropwise Et$_3$N (48 mL, 0.345 mol, 1.22 equiv.). After stirring at room temperature for 3 hours, TLC (Hexane CH$_2$Cl$_2$=90/10) indicated the reaction was complete. The suspension was filtered through a sintered glass funnel. The filtrate was diluted with 300 mL CH$_2$Cl$_2$, and then washed with 1 M NaOH (200 mL). The aqueous layer was extracted with another 300 mL CH$_2$Cl$_2$. The combined organic layer was washed with saturated NaHCO$_3$ (100 mL) and brine (100 mL), then dried over Na$_2$SO$_4$, filtered and concentrated to give a liquid as crude. The reaction mixture was purified through a silica gel plug eluting with (CH$_2$Cl$_2$/Hexane=3/2) to give 28 as a liquid (57.18 g, yield 84%). MS: 188 (M-56+1).

Step 2

To a solution of 4-fluorophenylacetonitrile (2.7 g, 10 mmol, 1 equiv.) in 30 mL DMSO, was added 60% NaH dispersion in mineral oil (0.88 g, 22 mmol, 2,2 equiv). After stirring at room temperature for 1.5 hours, the BOC aminodichloride 28 was added and stirred for 2 hours. The reaction mixture was poured into 150 g of ice. The mixture was extracted with CH$_2$Cl$_2$ (2×150 mL). The combined organic layer was washed with water (500 mL), dried over Na$_2$SO$_4$, filtered and concentrated to give 4.5 g of a liquid as the crude. The crude material was purified with flash chromatography column (EtOAc/Hexane=5/95) to give 29 as a liquid (1.83 g, yield 60%). MS: 305 (M+1).

Step 3

At 0° C., to a solution of 29 (1.69 g, 5.6 mmol, 1 equiv.) in 10 mL dry benzene, was added 12 mL of 1.0 M DIBAL (12 mmol, 2 equiv.) in hexane. After stirring at 0° C. for 30 min, the solution was warmed to room temperature. When the TLC (EtOAc/Hexane=1/4) indicated the reaction was complete, the reaction was quenched with 90 mL of 5% H$_2$SO$_4$. The aqueous layer was extracted with Et$_2$O(2×100 mL). The combined organic layer was dried over Na$_2$SO$_4$, filtered and concentrated to give 0.72 g of crude. The crude material was purified by flash column to give 30 as a liquid. (454 mg, yield 26%).

Step 4

At 0° C., a solution of aldehyde 30 (3.9 g, 12.8 mmol, 1 equiv.) in 10 mL EtOH was treated with NaBH$_4$ (580 mg, 15.3 mmol, 1.2 equiv.). After stirring at 0° C. for 30 min, the reaction was complete. The solvent was evaporated and the crude product was taken up with 10 mL saturated NaHCO$_3$, and extracted with CH$_2$CO$_2$ (2×120 mL). The combined organic layer was dried over Na$_2$SO$_4$, filtered and concentrated to give 31 as a solid (3.96 g, yield 100%).

Step 5

Using a procedure similar to the procedure described in Example 1, step 2, substituting 31 for 23 gave the compound of Example 31.

Example 32

Using a procedure similar to the one described in Example 1, step 3, gave the indicated compound.

Examples 33–39

Using a procedure similar to examples 4–10, respectively, substituting Example 32 for Example 1 gave the indicated compounds.

Examples 40

Dissolved the compound of Example 5 in MeOH saturated with NH$_3$, and stirred at 23° C. for 48 hours in a sealed tube. Evaporated the solvent to yield the target compound.

Examples 41–43

Using a procedure similar to that described in Example 40, substituting the compounds of Examples 6, 34, and 35 for the compound of Example 5, gave the compounds of Examples 41, 42, and 43 respectively.

Example 44

Step 1

Used a procedure similar to the EDC coupling procedure described in Example 2 using Boc-glycine as the corresponding carboxylic acid.

Step 2

Treated the product from Step 1 using a procedure similar to Example 1, step 3, gave the target compound.

Example 45

Dissolved compound 21 (15 mg, 0.03 mmol) in pyrrolidine (2 mL), and stirred at 23° C. for 48 hours. Evaporated the solvent to yield the target compound.

Examples 46–47

Using a procedure similar to the one described in Example 45 using methylamine and morpholine in place of pyrrolidine gave the compounds of Examples 46 and 47 respectively.

Examples 48–64

Compounds of the formula

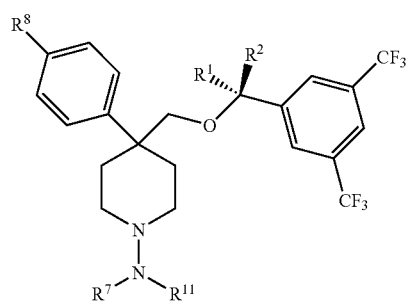

wherein R$^1$, R$^2$, R$^7$, R$^8$ and R$^{11}$ are described in Table 2 were prepared by the procedures described after Table 2.

TABLE 2

| Example Nos. | R$^8$ | R$^1$ | R$^2$ | —NR$^7$R$^{11}$ | LRMS (m + H) |
|---|---|---|---|---|---|
| 48 | H | H | H | 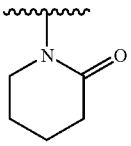 | 515.5 |
| 49 | H | H | H | 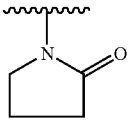 | 501.5 |
| 50 | H | H | H | 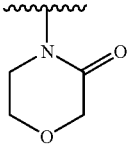 | 517.5 |

TABLE 2-continued
| Example Nos. | R⁸ | R¹ | R² | —NR⁷R¹¹ | LRMS (m + H) |
|---|---|---|---|---|---|
| 51 | H | H | H | 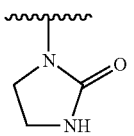 | 502.5 |
| 52 | F | H | H | 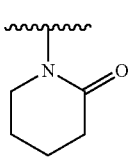 | 533.5 |
| 53 | F | H | H | 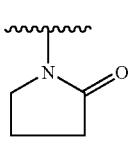 | 519.5 |
| 54 | F | H | H | 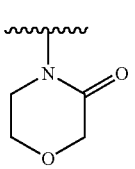 | 535.5 |
| 55 | H | H | H | 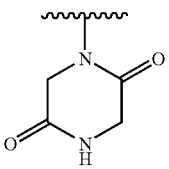 | 530.5 |
| 56 | H | H | CH₃ | 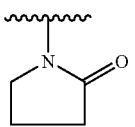 | 515.1 |
| 57 | H | H | CH₂OH | 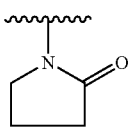 | 531.1 |
| 58 | H | H | H | 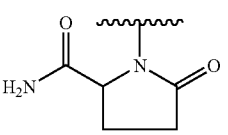 | 544.1 |
| 59 | H | H | H | 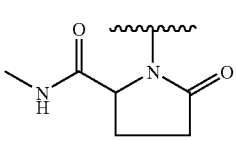 | 558.1 |
| 60 | H | H | H | 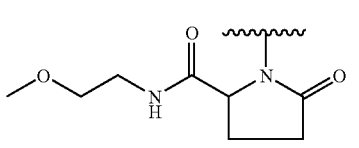 | 602.1 |

TABLE 2-continued

| Example Nos. | R[8] | R[1] | R[2] | —NR[7]R[11] | LRMS (m + H) |
|---|---|---|---|---|---|
| 61 | H | H | H | 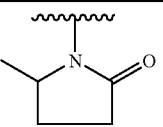 | 515.1 |
| 62 | H | H | H | 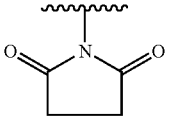 | 515.1 |
| 63 | H | H | H | 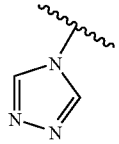 | 485.1 |
| 64 | H | H | H | 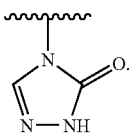 | 501.1 |

Example 48

Step 1

Using a procedure similar to the one described in Example 2 using 5-chlorovaleryl chloride in place of acetyl chloride gave the crude δ-chloroamide.

Step 2

Dissolved the crude δ-chloroamide from Step 1 (572 mg, 1.03 mmol) in anhydrous THF (10 mL), added sodium hydride (49 mg, 0.77 mmol) at 0° C. and stirred for 30 min. Heated at 60° C. for 3 hours. Removed the solvent, and quenched with saturated NaHCO₃ solution, and extracted with CH₂Cl₂ (2×15 mL). The combined organic layer was dried over MgSO₄ and concentrateded to yield a crude product. Purified with column chromatography using MeOH (sat. with NH₃) and CH₂Cl₂ (1:99) to afford the target compound.

Example 49

Used a procedure similar to the one described in Example 48, substituting 4-chlorobutyrylchloride for 5-chlorovaleryl chloride in Step 1. Proceeded as described in Example 48, step 2 to afford the target compound.

Example 50

Step 1

2-(2-chloroethoxy)ethanol was oxidized in the standard fashion with Jones reagent to give the corresponding carboxylic acid.

Step 2

Used a procedure similar to that described in Example 2, using the product of Step 1 as the carboxylic acid in a standard carbodiimide coupling.

Step 3

Using a procedure similar to Example 48, Step 2, provided the target compound.

Example 51

Step 1

Added saturated NaHCO₃ solution (2.78 g in 7 mL H₂O) to a solution of 2-amino ethanol (2 mL, 33.1 mmol) in THF (20 mL), and stirred at 0° C. for 40 min. Treated the reaction mixture with p-nitrophenyl chloroformate (7.0 g, 34.8 mmol) and stirred vigorously at 0° C. for additional 2 hours. Quenched with saturated NaHCO₃ solution, extracted with EtOAc (2×150 mL). The combined organic layer was dried over MgSO₄ and concentrated to yield a crude product. Purified on column chromatography using hexane and EtOAc (1:1) to give the product.

Step 2

To the product from Step 1 (900 mg, 4 mmol) in EtOAc (25 mL) at 0° C., was added saturated NaHCO₃ solution (25 mL), NaBr (445 mg, 4.4 mmol) and Tempo reagent (10 mg). Commercial bleach was added dropwise to the mixture with vigorous stirring at 0° C. over 20 min. Quenched with Na₂S₂O₃ (2 g) in H2O (10 mL), and added NaHCO₃ solution (20 mL). Extracted with EtOAc (2×100 mL), the combined organic layer was dried over MgSO₄ and concentrated to yield a crude product. Purified on column chromatography using hexane and EtOAc (1:1) to give the product.

Step 3

Dissolved the product from Step 2 (100 mg, 0.45 mmol) and Example 1 (202 mg, 0.45 mmol) in THF, and treated with NaBH₃CN (57 mg, 0.9 mmol) at 23° C. Heated at 60° C. for an additional 18 hours, and quenched with saturated NaHCO₃ solution. Extracted with EtOAc (2×150 mL). Dried the combined organic layer over MgSO₄ and concentrated to yield a crude product. Purified on column chromatography using MeOH (sat. with NH$_3$) and CH$_2$Cl$_2$ (1:99) to give the target compound.

Examples 52–54

Prepared the target compounds using a procedure similar to those used to prepare the compounds of Examples 48–50 substituting the compound of Example 32 for the compound of Example 1.

Example 55

Step 1

Dissolved Example 44 in CH$_2$Cl$_2$, and used a procedure similar to that described for Example 2 using chloride acetyl chloride in place of acetyl chloride to provide the β-amido-δ-chloro amide.

Step 2

Used a procedure similar to Example 48, Step 2, to provide the target compound.

Example 56

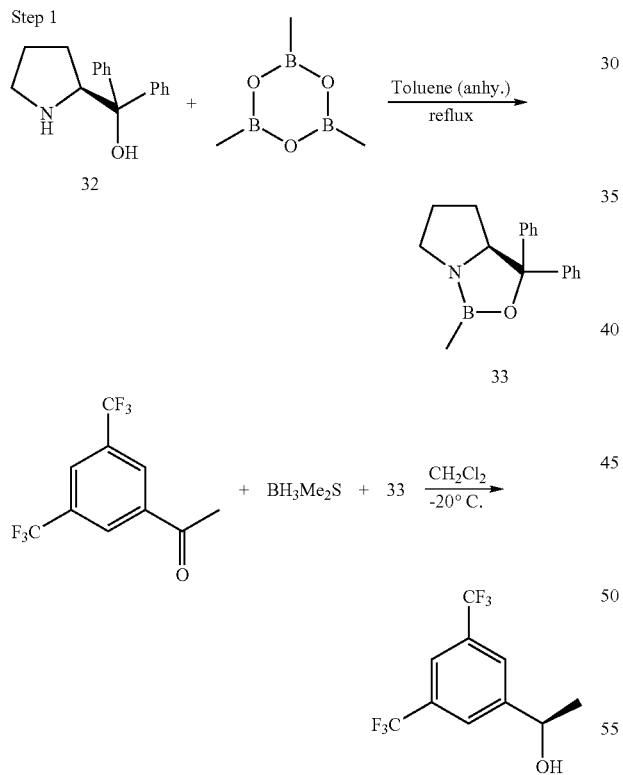

A flame-dried 50 mL one-necked flask was charged with 5.10 g (20.1 mmol, 1.0 eq) of S-diphenylprolinol (32) and 56 mL of anhydrous toluene. The solution was heated up to 140–150° C. 36 mL of dry toluene was azeotropically distilled through a Dean-Stark trap with an air condenser. Another 36 mL of toluene was added and the azeotropic distillation was repeated three times. After the third azeotropic distillation was done, another 36 mL of anhydrous toluene was added. The solution was allowed to cool to room temperature. Methylboroxin (1.90 mL, 13.5 mmol, 0.67 eq) was added via syringe over 5 min. A solid was formed after completion of the addition. The reaction mixture was stirred at room temperature for 30 min and 36 mL of toluene was distilled off. Another 36 mL of dry toluene was added and distilled off again. The distillation was repeated one more time, then 20 mL of 1.0 M of CBS catalyst (33) solution in toluene was prepared. The solution was used in CBS reduction directly.

Step 2

A 1 L oven-dried round-bottomed flask was charged with 102.14 g (0.4 mol, 1.0 eq) of 3',5'-Bis(trifluoromethyl) acetophenone and 780 mL of anhydrous dichloromethane. The resultant solution was transferred into a dry dropping funnel. An oven-dried 3 L round-bottomed flask was cooled to −20° C., and 20 mL of 1.0 M CBS catalyst (33) toluene solution was added via syringe, followed by 40 mL of 10.0–10.3 M borane-methylsulfide complex. The 3',5'-Bis (trifluoromethyl)-acetophenone solution was added dropwise through the dropping funnel. The addition was carried out over 2 days. During the addition, the temperature was maintained at −20° C. with a cooling machine. Once the addition was finished, the reaction was monitored by TLC (EtOAc/Hexane=1/4). When the starting material was completely consumed, 250 mL of methanol was added slowly. Hydrogen gas was emitted. The reaction solution was then concentrated to give a solid. The solid was dissolved in 500 mL of diethyl ether, then 45 mL of 2.0 M of hydrochloric acid in diethyl ether was added slowly at −20° C. A precipitate was formed. The reaction mixture was Warmed to room temperature and stirred for 30–40 min. The mixture was filtered through a funnel and the filtrate was concentrated to give 101.5 g of a solid of 34 (yield 98.7%). Chiral HPLC Chiral OD(Chiralcel) column (Hexane/IPA=98/2) showed 94.6%.

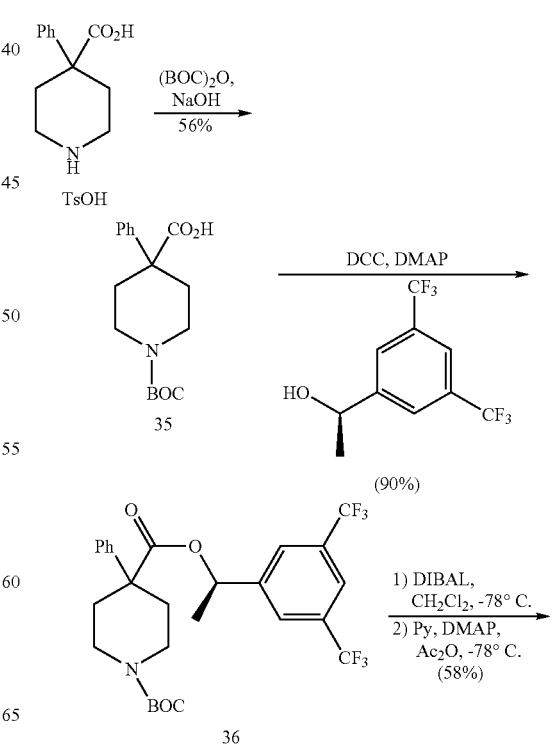

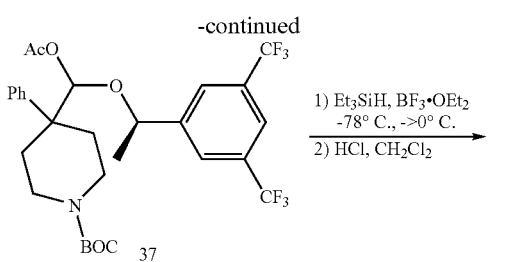

Step 3

A mixture of amino-acid (20 g, 53.0 mmol, 1 equiv.) and di-tert-butyl dicarbonate (23.13 g, 106.0 mmol, 2 equiv.) in dichloromethane (250 mL), THF(250 mL) and water(100 mL) was stirred vigorously while 80 mL of 1 N NaOH solution was added dropwise over a period of 25 min. The resultant suspension was stirred at room temperature overnight. The reaction mixture was neutralized with 1 N HCl to pH 5, then extracted with $CH_2Cl_2$ (400 mL×2). The organic layer was dried over $Na_2SO_4$, filtered and concentrated to a solid as crude, which upon recrystallization in $Et_2O$, gave 9 g of 35 as a solid (yield 56%) MS: 306.1 (M+1).

Step 4

At 0° C., to the suspension of 35 (7.15 g, 23.3 mmol, 1.2 equiv.) in 60 mL of anhydrous toluene and 10 mL of dry $CH_2Cl_2$, was slowly added DCC (5.76 g, 27.9 mmol, 1.4 equiv.). After stirring at 0° C. and room temperature each for 20 min, the thick solution was treated at 0° C. with methyl-bis(triflouromethyl)benzyl alcohol 34 (5 g, 19.4 mmol, 1 equiv.), and DMAP (2.37 g, 19.4 mmol, 1 equiv.). Stirring at room temperature till TLC(Hexane/EtOAc 3/2) indicated the complete consumption of 34. The reaction mixture was then concentrated and purified with flash chromatography column (Hexane→Hexane/EtOAc 90/10 gradient) to give 36 as a liquid (yield 90%). MS: 546 (M+1).

Step 5

10 mL of precooled 1.0 M DIBAL solution in hexane was added slowly at −78° C. via cannula to a solution of 36 (2.48 g, 4.55 mmol, 1 equiv.) in 25 mL of anhydrous $CH_2Cl_2$, After stirring at −78° C. until TLC (Hexane/EtOAc 3/2) showed complete consumption of 36, were added 1.1 mL of dry pyridine, a solution of DMAP(1.1 g, 9 mmol, 2 equiv.) in 9 mL of dry $CH_2Cl_2$, and 2.58 mL of $Ac_2O$. The reaction solution was stirred at −78° C. for 15 hours, then warmed to −10° C. and stirred for another 2 hours before it was quenched by slowly adding saturated $NH_4Cl$ solution (35 mL) and saturated sodium potassium tartrate solution(35 mL). The mixture was stirred at room temperature for 30 min and extracted with $CH_2Cl_2$ (3×125 mL). The combined organic layer was washed with 1M $NaHSO_4$(2×35 mL), saturated $NaHCO_3$(2×100 mL), and brine(100 mL), then dried over $Na_2SO_4$, filtered and concentrated to give 2.71 g of a liquid as crude. Further purification by flash chromatography eluting with (Hexane→Hexane/EtOAc 97/3 gradient with 2% $Et_3N$) gave 37 as a liquid (1.55 g, yield 58%).

Step 6

A solution of acetoxy ether 37 (1.48 g, 2.51 mmol, 1 equiv.) in 40 mL of dry $CH_2Cl_2$ was treated with triethylsilane (2.67 mL, 16.7 mmol, 6.5 equiv.) and $BF_3 \cdot Et_2O$ (0.57 mL., 4.50 mmol, 1.79 equiv.) at −78° C. The solution was stirred overnight while the temperature was raised to 0° C. When TLC (Hexane/EtOAc 90/10+2% $Et_3N$) showed complete consumption of 37, the reaction was quenched with saturated $NaHCO_3$ (40 mL). The aqueous layer was extracted with $CH_2Cl_2$ (2×150 mL). The combined organic layer was dried over $Na_2SO_4$, filtered and concentrated to give a liquid. The crude was dissolved in 20 mL of $CH_2Cl_2$, and treated with 6.28 mL of 4.0 N HCl in 1,4-dioxane to give 826.4 mg of a solid as 38. MS: 432 (M+1).

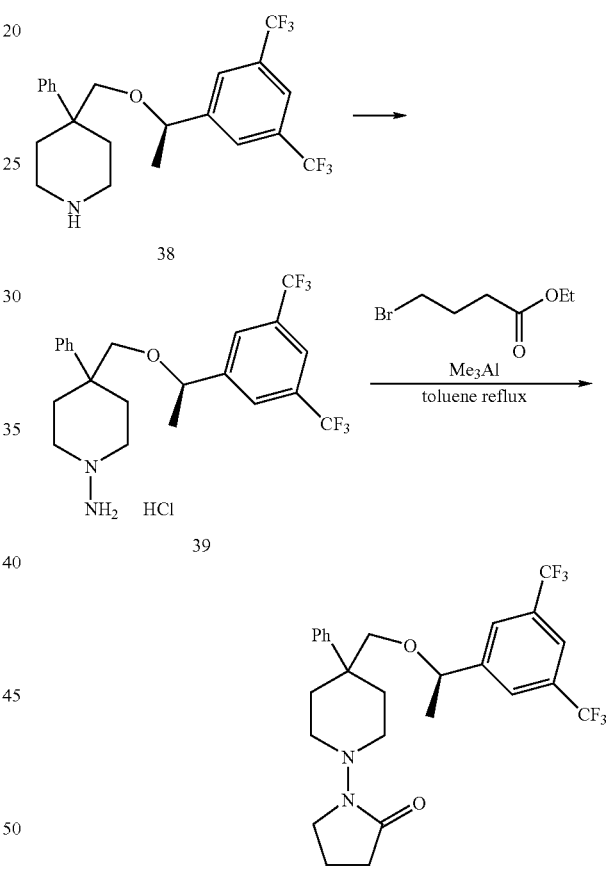

Example 56

Step 7

The hydrochloride salt (38) was neutralized as described in Example 1, Step 3. Use a procedure similar to Example 1, Step 4–5 to provide the aminopiperidine 39.

Step 8

A solution of amino-piperidine 39 (600 mg, 1.24 mmol, 1 equiv.) in 20 mL dry toluene was treated with 0.75 mL of 2.0 M trimethylaluminum solution in toluene. After stirring at room temperature for 30 min, the solution was heated to 125° C., then treated-with 0.18 mL of ethyl 4-bromobutyrate. The mixture was heated to reflux for 3.5 hours (TLC (MeOH/CH$_2$Cl$_2$=5:95)), whereupon it was quenched with 15 mL saturated sodium potassium tartrate and diluted with 100 mL of EtOAc. The aqueous layer was further extracted with EtOAc (2×50 mL). The combined organic layer was washed with brine (100 mL), dried over NaSO4, filtered and concentrated to give 750 mg crude. Purification on flash column (CH$_2$Cl$_2$→CH$_2$Cl$_2$/MeOH=95/5 gradient) gave compound 56 as a liquid (442 mg, yield 69%).

Example 57

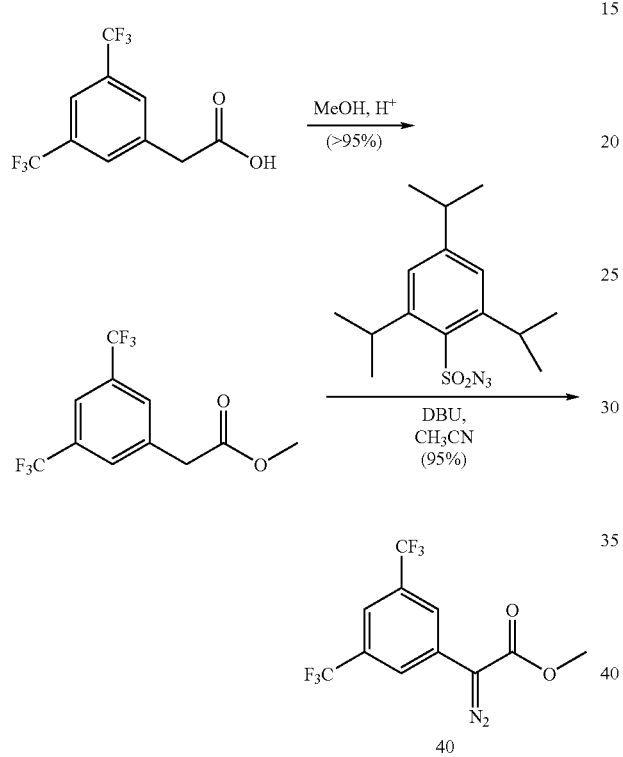

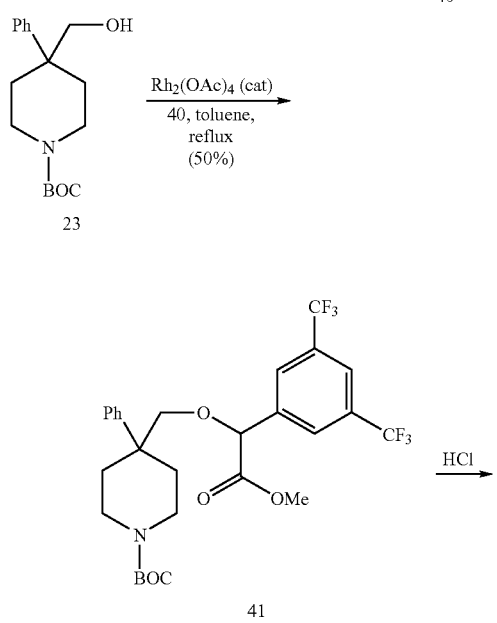

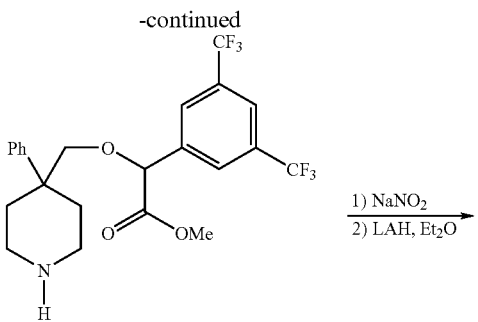

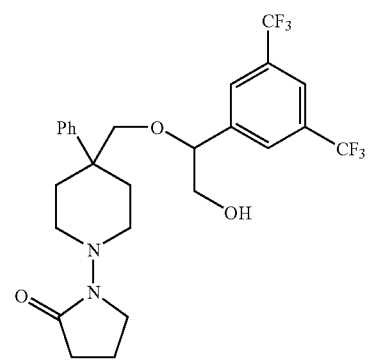

Example 57

Step 1

A solution of 3,5-bis(triflouromethyl)phenylacetic acid in MeOH was refluxed overnight with a catalytic amount of concentrated H$_2$SO$_4$. The solvent was evaporated, taken up with Et$_2$O and washed with saturated NaHCO$_3$. The organic layer was dried over Na$_2$SO$_4$, filtered and concentrated to give the methyl 3,5-bis(triflourompethyl)phenylacetate as a liquid. (yield 95%).

Step 2

A solution of methyl 3,5-bis(triflouromethyl)phenylacetate (2.18 g, 7.62 mmol, 1 equiv.) in 12.5 mL dry CH$_3$CN was treated with 2,4,6-triisopropyl benzenesulfonyl azide (2.65 g, 8.56 mmol, 1.12 equiv.), and 1.26 mL of DBU at −9° C. After stirring at about −8 to −5° C. for 1.5 hours, the solution was stirred at room temperature for another 1 hour. The solution was concentrated and purified on column (Hexane/EtOAc=97/3) to afford the product 40 (2.27 g, yield 96%).

Step 3:

To a solution of 23 (Example 1, Step 1) (2.92 g, 10 mmol, 1.74 equiv.) and Rhodium (II) acetate (5 mg, 0.011 mmol, 0.2% equiv.) in 5 mL of dry benzene, was added a solution of diazo-ester 40 (1.8 g, 5.77 mmol, 1 equiv.) in 2.6 mL dry benzene through syringe pump at a rate of 0.09 mL/h. The addition was done over 29 hours. The reaction mixture was stirred for another 30 min until TLC ($Et_2O$/Hexane=25%) showed 40 was completely consumed. The solvent was evaporated and purified on column (Hexane/$Et_2O$=3:1→3: 2) to give the product 41 as a liquid (1.64 g, yield 49%).

Step 4

The Boc protected piperidine was deprotected and neutralized in a similar fashion to Example 1, Step 3 to provide the corresponding piperidine.

Step 5

Used a procedure similar to Example 1, Steps 4–5, to provide aminopiperidine 43.

Step 6:

Used a procedure similar to Example 49, to provide the target compound.

Example 58

Step 1

A suspension of 1 hydrochloride (2.0 g) in 1,2 dichloroethane (15 mL) was treated with dimethyl-2-oxo-glutarate (0.65 mL) and $NaB(OAc)_3H$ (1.27 g). Gas evolution ensued whereupon HOAc (0.75 mL) was added. The resultant solution was stirred at 23° C. for 1 h whereupon additional $NaB(OAc)_3H$ (2 g) was added. The mixture was stirred for 14 h, then poured into sat. $NaHCO_3$ (40 mL), and extracted with $CH_2Cl_2$ (2×150 mL). The combined organic layers were washed with brine (40 mL), dried ($Na_2SO_4$) and concentrated to give the crude as an oil (2.51 g).

Step 2:

The crude material from Step 1 was dissolved in dry toluene (100 mL), heated to 115° C., and treated with $Me_3Al$ (2.14 mL of 2 M in toluene). The resultant solution was stirred for 5 h whereupon additional $Me_3Al$ (2.14 mL of 2 M in toluene) was added. The mixture was stirred further until TLC ($CH_2Cl_2$/MeOH 95/5) indicated near complete reaction. The mixture was diluted with EtOAc (200 mL), cooled to 0° C., and quenched with sat sodium-potassium tartrate (100 mL). After stirring at 0° C. for 30 min, the layers were separated, and the aqueous layer was extracted with EtOAc (200 mL). The combined organic layers were washed with brine (100 mL), dried ($Na_2SO_4$), and concentrated to give the crude. Purification by silica gel chromatography (hexane→hexane/EtOAc 1:1) provided 615 mg (26%) of the lactam ester.

Step 3

Used a procedure similar to that used in Example 40, substituting the lactam ester product of Step 2 above for 5 to give 58.

Examples 59–60

Used a procedure similar to that used in Example 58 but substituted methylamine and $MeOCH_2CH_2NH_2$ for ammonia in Step 3 to afford 59 and 60 respectively.

Example 61

Used a procedure similar to that used in Example 58, Steps 1–2, using methyl levulinate in place of dimethyl-2-oxo-glutarate to give the target compound.

Example 62

A solution of 1 hydrochloride (500 mg) in dry toluene (100 mL) was treated with succinic anhydride (133 mg) and TsOH (60 mg) and heated to reflux with a Dean Stark trap for 96 h. The reaction mixture was concentrated in vacuo and purified by silica gel chromatography (hexane/EtOAc 2:1→hexane/EtOAc 1:1) to give 167 mg of the target compound.

Example 63

A solution of 1 hydrochloride (500 mg) and 1,2-diformylhydrazine (226 mg) in dry pyridine (10 mL) was dried by azeotropic distillation under reduced pressure (2×10 mL pyridine). Pyridine (5 mL) was added, followed by TMSCl (2 mL) and $NEt_3$. The resultant solution was stirred at 80° C. for 2.5 d, whereupon it was concentrated in vacuo, dissolved in $CH_2Cl_2$ (50 mL) and washed with sat $NaHCO_3$ (15 mL). The aqueous layer was extracted with $CH_2Cl_2$ (50 mL) and the combined organic layers were washed with 2N HCl (15 mL)/brine (5 mL), dried ($Na_2SO_4$), and concentrated to give the crude. Purification by silica gel chromatography (hexane/EtOAc 1:1→EtOAc) provided 220 mg (43%) of the target compound.

Example 64

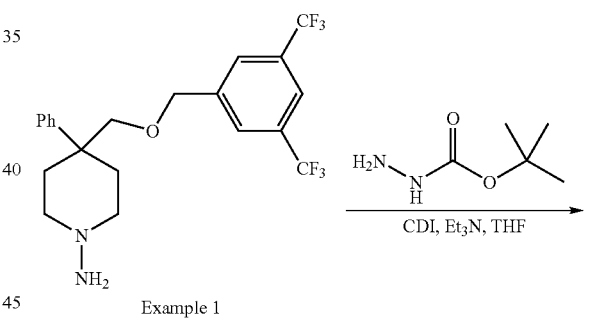

Example 1

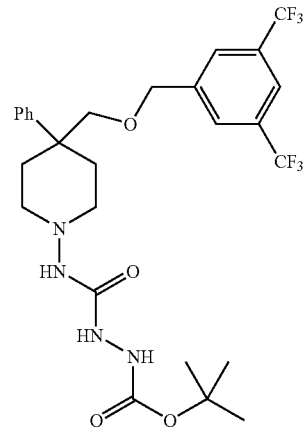

44

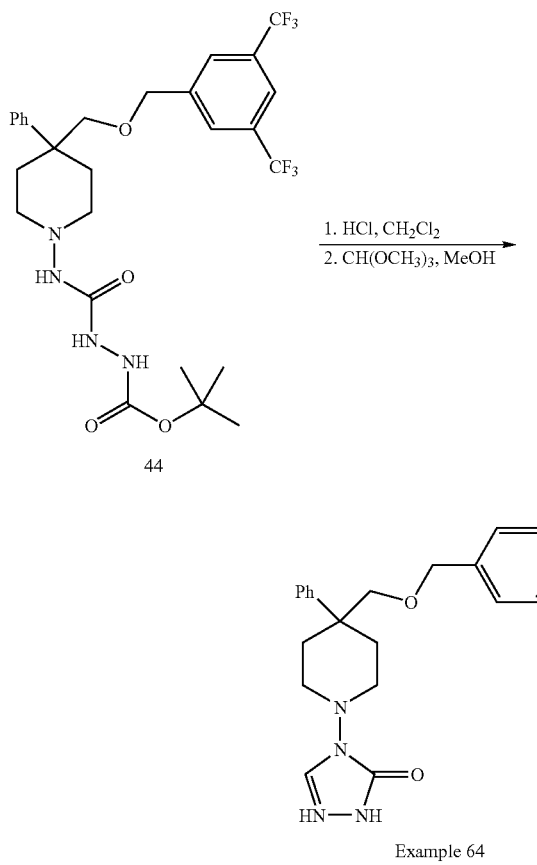

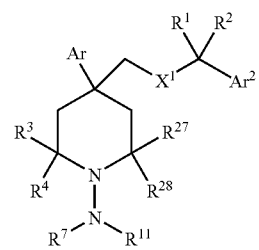

Example 64

Step 1

To a 50 mL round bottom flask was added t-butyl carbazate (0.155 g, 1.17 mmol, 1.1 equiv.) and THF (4 mL). To the resulting colorless solution was added CDI (0.207 g, 1.28 mmol, 1.2 equiv.) and a few 3 Å molecular sieves, and the reaction mixture was stirred at about 23° C. for about 18 hours. Triethyl amine (0.18 mL 28 mmol, 1.2 equiv.) was added to the reaction mixture followed by addition of Example 1 (0.5 g, 1.02 mmol, 1 equiv.). The reaction mixture turned into a white suspension. The reaction mixture was stirred at about 23° C. for about 0.5 hour. The reaction mixture was purified using Biotage (CH$_2$Cl$_2$, then 2% MeOH/CH$_2$Cl$_2$) to give 0.23 g of compound 44.

Step 2

To a solution of compound 44 (0.1 g, 0.17 mmol, 1 equiv.) in CH$_2$Cl$_2$ (10 mL) was added a solution of 4 M HCl in dioxane (0.5 mL, 2 mmol, 11.78 equiv.). The reaction mixture was stirred at about 23° C. for about 3 hours. The solvent was then evaporated. MeOH was added to the residue followed by a solution of trimethyl orthoformate (0.5 mL) in MeOH (0.3 mL). The reaction mixture was stirred at about 23° C. for about 18 hours. The reaction mixture was then concentrated and purified by column chromatography (hexane, then 40% EtOAc/hexane) to afford the product Example 64. LCMS (M+H)+501.1.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound having the formula (I):

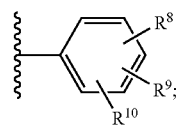

(I)

or a pharmaceutically acceptable salt or solvate thereof, wherein

Ar$^1$ and Ar$^2$ are each independently selected from the group consisting of (R$^{19}$)$_{n7}$-heteroaryl- and

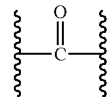

X$^1$ is selected from the group consisting of —O—, —S—, —SO—, —SO$_2$—, —NR$^{12}$—, —N(CONR$^{12}$)— and —N(SO$_2$R$^{15}$)—;

R$^1$, R$^3$ and R$^5$ are each independently selected from the group consisting of H and C$_1$–C$_6$ alkyl;

R$^2$, R$^4$ and R$^6$ are each independently selected from the group consisting of H, —CONR$^{13}$R$^{14}$ and —(CH$_2$)$_{n1}$-G; wherein G is selected from the group consisting of H, —CF$_3$, —CHF$_2$, —CH$_2$F, —OH, —O—(C$_1$–C$_6$) alkyl, —SO$_2$R$^{13}$, —O—(C$_3$–C$_8$ cycloalkyl), —NR$^{13}$R$^{14}$, —SO$_2$NR$^{13}$R$^{14}$, —NR$^{13}$SO$_2$R$^{15}$, —NR$^{13}$COR$^{12}$, —NR$^{12}$(CONR$^{13}$R$^{14}$). —CONR$^{13}$R$^{14}$, —COOR$^{12}$ and C$_3$–C$_8$ cycloalkyl; or R$^1$ and R$^2$, taken together with the carbon to which they are attached, form a C$_3$–C$_8$ cycloalkyl ring; or R$^1$ and R$_2$, taken together with the carbon to which they are attached, form a

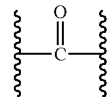

group; or

R$^3$ and R$^4$, taken together with the carbon to which they are attached, form a

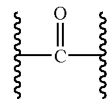

group; or

R$^5$ and R$^6$, taken together with the carbon to which they are attached, form a

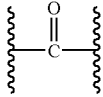

group;

R[7] and R[11] are each independently selected from the group consisting of H, $C_1$–$C_6$ alkyl, $C_3$–$C_8$ cycloalkyl, $(R^{16})_{n7}$-aryl-, $(R^{19})_{n7}$-heteroaryl-, —COOR[29], —CONR[21]R[22], —CON(R[21])(CH$_2$)$_n$-G[1], —S(O)$_{n5}$(CH$_2$)$_n$-G[1], —S(O)$_{n5}$R[13], —CO(CH$_2$)$_n$-G[1] and —(CH$_2$)$_{n1}$-G[1]; wherein n is 0–4, and G[1] is selected from the group consisting of H, —OH, $(C_1$–$C_5)$alkyl, —O—$(C_1$–$C_6$alkyl), —S(O)$_{n5}$R[13], —O—$(C_3$–$C_8\ cycloalkyl)$, —NR[13]R[14], —SO$_2$NR[13]R[14], —NR[13]SO$_2$R[15], —NR[13]COR[12], —NR[12](CONR[13]R[14]), —OC(=O)R[12], —CONR[13]R[14], —COOR[12], $C_3$–$C_8$ cycloalkyl, —CF$_3$, $(R^{16})_{n7}$-aryl-O—, $(R^{16})_{n7}$-aryl-, $(R^{19})_{n7}$-heteroaryl-, $(R^{19})_{n7}$-heterocycloalkyl- and alkenyl, and provided that, when n is 0, then G[1] is selected from the group consisting of H, $(C_1$–$C_6)$alkyl, alkenyl, —CONR[13]R[14], —COOR[12], $C_3$–$C_8$ cycloalkyl, —CF$_3$, $(R^{16})_{n7}$-aryl-, $(R^{19})_{n7}$-heteroaryl-, and $(R^{19})_{n7}$-heterocycloalkyl-; and provided that, when $n_1$ is 1, then G[1] is selected from the group consisting of H, $(C_1$–$C_6)$alkyl, alkenyl, —S(O)$_{n5}$R[13], —SO$_2$NR[13]R[14], —CONR[13]R[14], —COOR[12], $C_3$–$C_8$ cycloalkyl, —CF$_3$, $(R^{16})_{n7}$-aryl-, $(R^{19})_{n7}$-heteroaryl- wherein said heteroaryl ring is bound by a ring carbon to the —(CH$_2$)$_{n1}$- group, and $(R^{19})_{n7}$-heterocycloalkyl- wherein said heterocycloalkyl ring is bound by a ring carbon to the —(CH$_2$)$_{n1}$— group; or R[7] and R[11], taken together with the nitrogen to which they are attached, form a 5–7 membered heterocycloalkyl ring of the following formula:

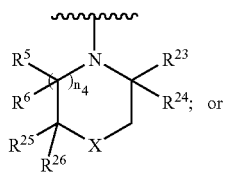

R[7] and R[11], taken together with the nitrogen to which they are attached, form a 5-membered ring having the formula (A) or (B):

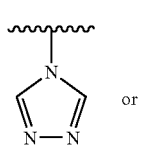

(A)

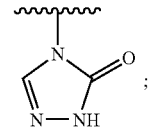

(B)

X is selected from the group consisting of —NR[20]—, —N(CONR[13]R[14])—, —N(CO$_2$R[13])—, —N(SO$_2$R[15])—, —N(COR[12])—, —N(SO$_2$NHR[13])—, —O—, —S—, —SO—, —SO[2]—, —CF$_2$—, —CH$_2$—, and C(R[12])F—;

R[8], R[9] and R[10] are each independently selected from the group consisting of H, $C_1$–$C_6$ alkyl, $C_3$–$C_8$ cycloalkyl, —OR[12], halogen, —CN, —NO$_2$, —CF$_3$, —CHF$_2$, —CH$_2$F, —OCF$_3$, —OCHF$_2$, —OCH$_2$F, —COOR[12], —CONR[21]R[22]; —NR[21]COR[12], —NR[21]CO$_2$R[15], —NR[21]CONR[21]R[22], —NR[21]SO$_2$R[15], —NR[21]R[22], —SO$_2$NR[21]R[22], —S(O)$_{n5}$R[15], $(R^{16})_{n7}$-aryl- and $(R^{19})_{n7}$-heteroaryl-;

R[12] is selected from the group consisting of H, $C_1$–$C_6$ alkyl and $C_3$–$C_8$ cycloalkyl;

R[13] and R[14] are each independently selected from the group consisting of H, $C_1$–$C_6$ alkyl, $C_2$–$C_3$ alkyl-O—CH$_3$, $C_3$–$C_8$ cycloalkyl, $(R^{19})_{n7}$-aryl(CH$_2$)$_{n6}$- and $(R^{19})^{n7}$-heteroaryl-(CH$_2$)$_{n6}$-; or R[13] and R[14], taken together with the nitrogen to which they are attached, form a 4–7 membered ring containing from 0–3 additional heteroatoms selected from the group consisting of —O—, —S— and —NR[12]—;

R[15] is $C_1$–$C_6$ alkyl, $C_3$–$C_8$ cycloalkyl or —CF$_3$;

R[16] is 1 to 3 substituents each independently selected from the group consisting of $C_1$–$C_6$ alkyl, $C_3$–$C_8$ cycloalkyl, $C_1$–$C_8$ alkoxy, halogen and —CF$_3$;

R[19] is 1 to 3 substituents each independently selected from the group consisting of $C_1$–$C_6$ alkyl, $C_3$–$C_8$ cycloalkyl, —OH, halogen, —CN, —NO$_2$, —C(O)CF$_3$, —CF$_3$, —CHF$_2$, —CH$_2$F, —OCF$_3$, —OCHF$_2$, —OCH$_2$F, —O—$(C_1$–$C_6$ alkyl), —O—$(C_3$–$C_8$ cycloalkyl), —COOR[2], —CONR[21]R[22], —NR[21]R[22], —NR[21]COR[12], —NR[21]CO$_2$R[12], —NR[21]CONR[21]R[22], —NR[21]SO$_2$R[15] and —S(O)$_{n5}$R[15];

R[20] is H, $C_{1–C6}$ alkyl, $C_3$–$C_8$ cycloalkyl, —(CH$_2$)$_{n6}$-heterocyclalkyl, $(R^{19})_{n7}$-aryl(CH$_2$)$_{n6}$— or $(R^{19})_{n7}$-heteroaryl- (CH$_2$)$_{n6}$-;

R[21] and R[22] are each independently selected from the group consisting of H, $C_1$–$C_6$ alkyl, $C_3$–$C_8$ cycloalkyl and benzyl; or R[21] and R[22], taken together with the nitrogen to which they are attached, form a 4–7 membered heteroaryl ring containing from 0–3 additional heteroatoms selected from the group consisting of —O—, —S— and NR[12]—;

R[23] and R[24] are each independently selected from the group consisting of H, $C_1$–$C_6$ alkyl and —CONR[13]R[14]; or R[23] and R[24], taken together with the carbon atom to which they are attached, form a

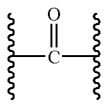

group;

R²⁵, R²⁶, R²⁷ and R²⁸ are each independently selected from the group consisting of H and $C_1$–$C_6$ alkyl; or
R²⁵ and R²⁶, taken together with the carbon atom to which they are attached, form a

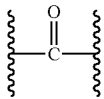

group; or

R²⁷ and R²⁸, taken together with the carbon atom to which they are attached, form a

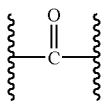

group;

R²⁹ is selected from the group consisting of $C_1$–$C_6$ alkyl and $C_3$–$C_8$ cycloalkyl;

$n_1$ is 1–4,
$n_4$ is 0–2,
$n_5$ is 0–2,
$n_6$ is 0–3,
$n_7$ is 0–3, and provided that, when $n_4$ is 0, and R²⁵ and R²⁶ are each H, then X is not —O—, —NR²⁰— or —S—.

2. The compound of claim 1 wherein $X^1$ is —O—.

3. The compound of claim 1 wherein $Ar_1$ and $Ar^2$ are each independently

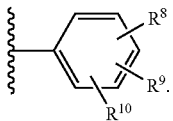

4. The compound of claim 3 wherein R⁸, R⁹ and R¹⁰ are each independently selected from the group consisting of H, —CH₃, halogen and —CF₃.

5. The compound of claim 1 wherein
$X^1$ is —O—; and
$Ar^1$ and $Ar^2$ are each independently

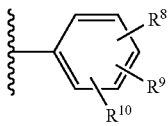

wherein R⁸, R⁹ and R¹⁰ are each independently selected from the group consisting of H, —CH₃, halogen and —CF₃.

6. The compound of claim 1 wherein $Ar^1$ is

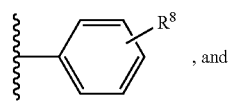, and $Ar^2$ is

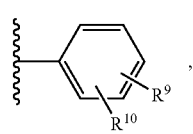, wherein,
R⁸ is selected from the group consisting of H and F, and
R⁹ and R¹⁰ are each independently selected from the group consisting of H, —CH₃, F, Cl and —CF₃.

7. The compound of claim 6 wherein
$X^1$ is —O—; and
R³, R⁴, R²⁷ and R²⁸ are each H.

8. The compound of claim 6 wherein R⁵ and R⁶ are H.

9. The compound of claim 7 wherein R⁷ and R¹¹, taken together with the nitrogen to which they are attached, form a 5–7 membered ring having the following formula:

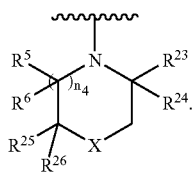

10. The compound of claim 1 having the formula

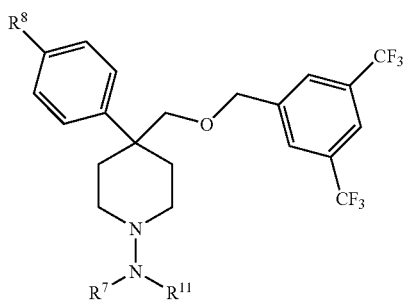

wherein R⁷, R⁸ and R¹ are selected from the group consisting of:

| R⁸ | R⁷ | R¹¹ |
|---|---|---|
| H | H | H |
| H | H | ![acyl] |

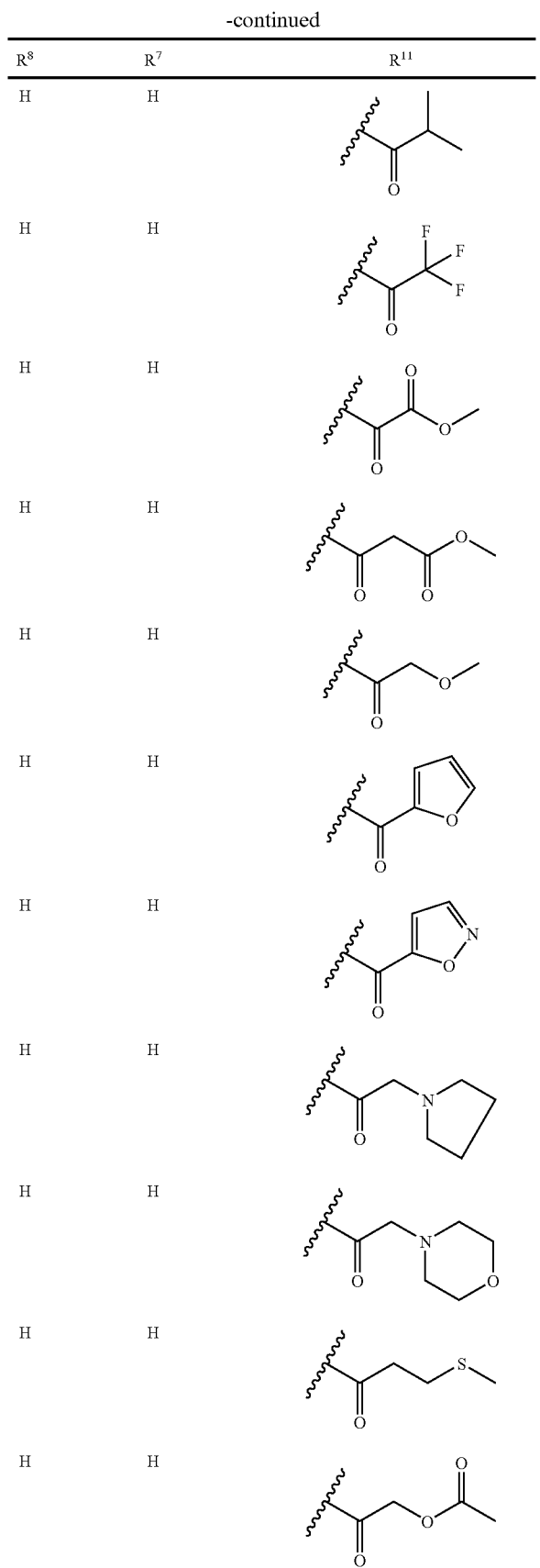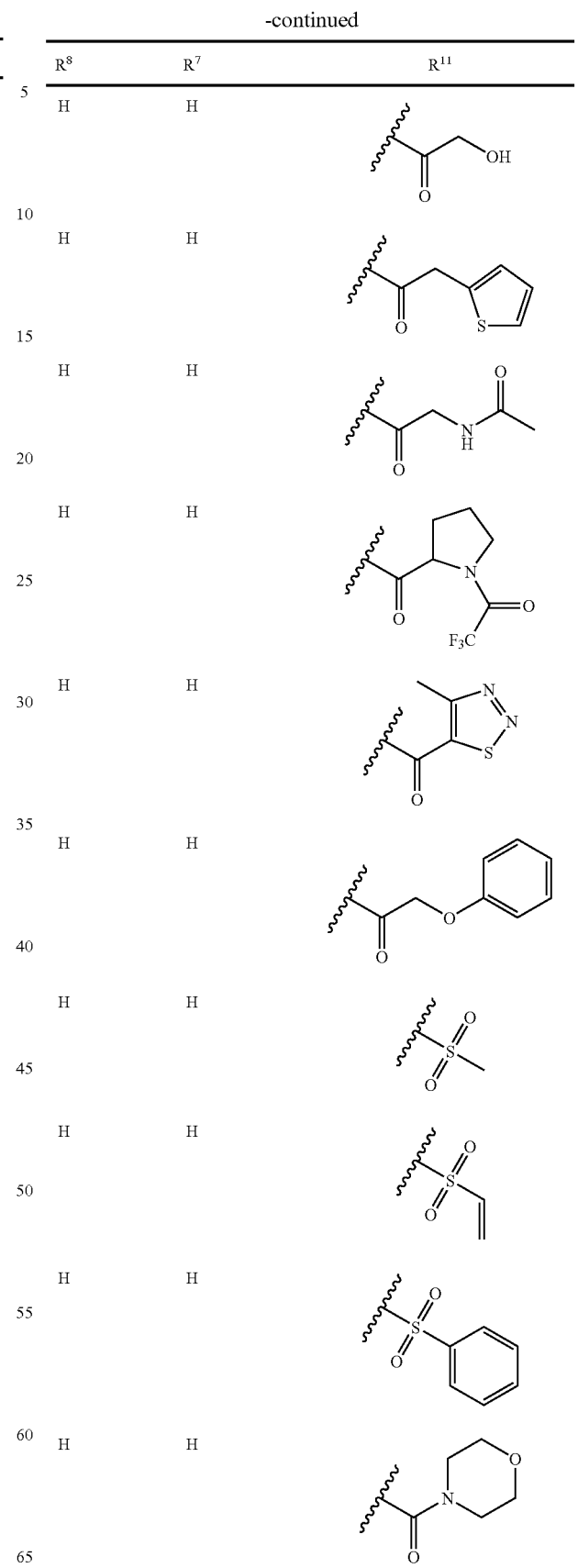

-continued
| R⁸ | R⁷ | R¹¹ |
|---|---|---|
| H | H | 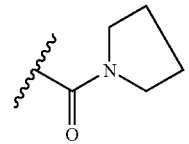 |
| H | H | 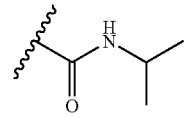 |
| H | H | 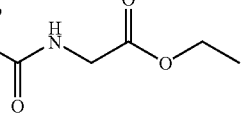 |
| H | H | 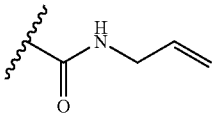 |
| H | H | 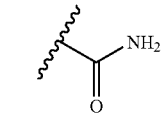 |
| H | 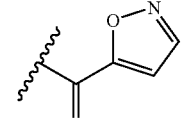 | 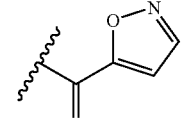 |
| H | 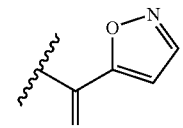 | 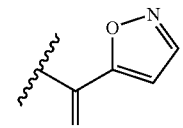 |
| F | H | 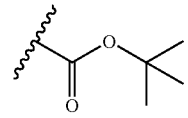 |
| F | H | H |
| F | H | 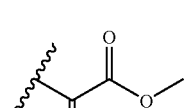 |
| F | H | 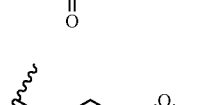 |
-continued
| R⁸ | R⁷ | R¹¹ |
|---|---|---|
| F | H | 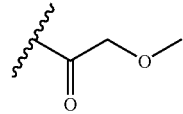 |
| F | H | 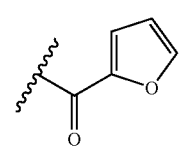 |
| F | H | 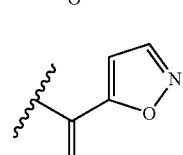 |
| F | H | 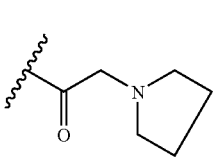 |
| H | H | 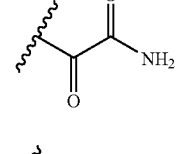 |
| H | H | 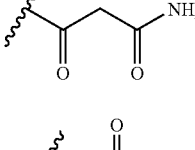 |
| F | H | 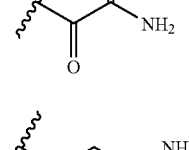 |
| F | H | 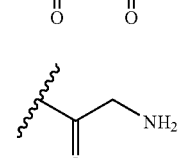 |
| H | H | 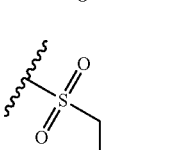 |
| H | H | 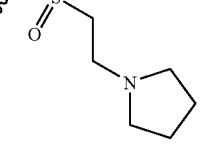 |

-continued
| $R^8$ | $R^7$ | $R^{11}$ |
|---|---|---|
| H | H | 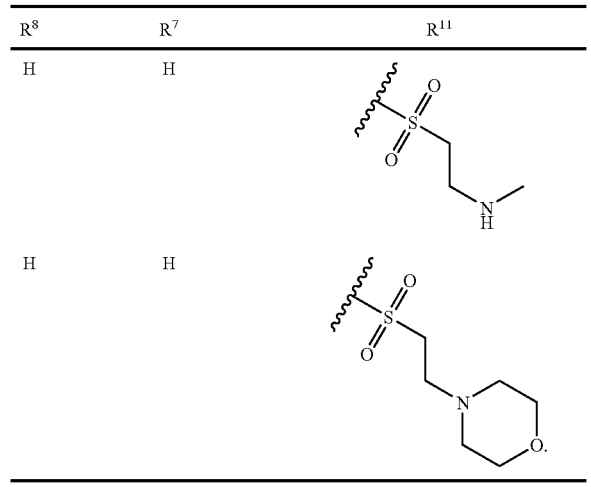 |
| H | H | |
11. The compound of claim 1 having the formula:
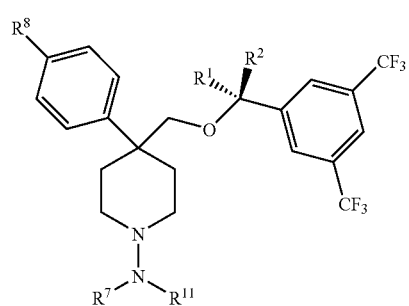
wherein $R^1$, $R^2$, $R^7$, $R^8$ and $R^1$ are selected from the group consisting of:
| $R^8$ | $R^1$ | $R^2$ | —$NR^7R^{11}$ |
|---|---|---|---|
| H | H | H | 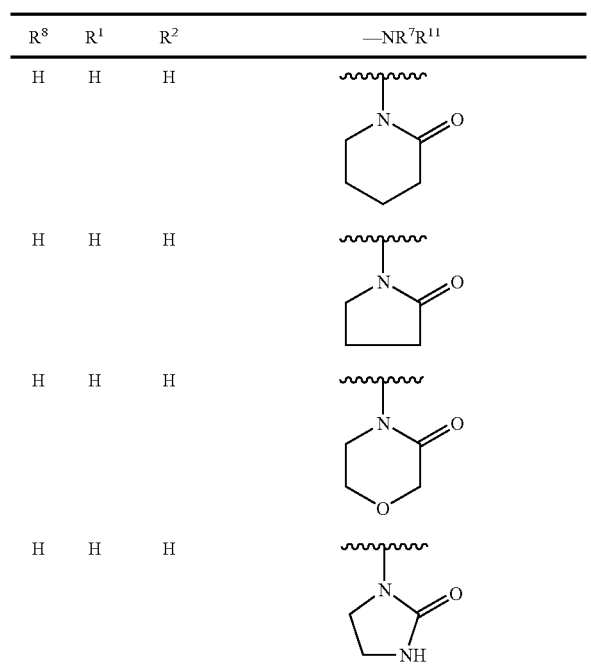 |
| H | H | H | |
| H | H | H | |
| H | H | H | |
-continued
| $R^8$ | $R^1$ | $R^2$ | —$NR^7R^{11}$ |
|---|---|---|---|
| F | H | H | 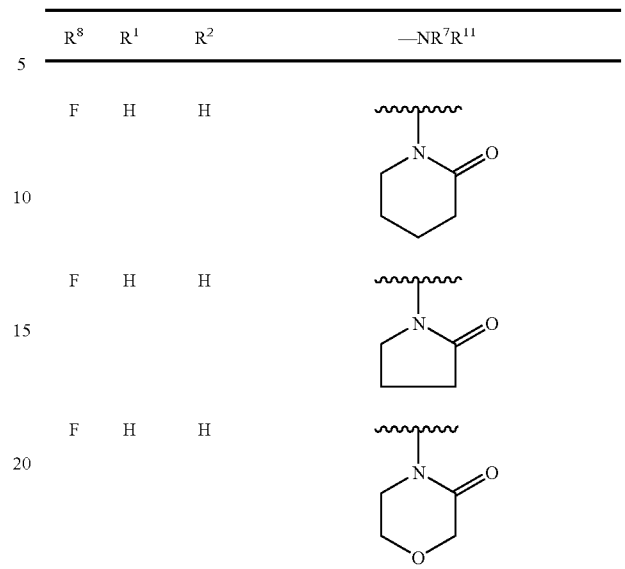 |
| F | H | H | |
| F | H | H | |
| H | H | H | |
| H | H | CH$_3$ | |
| H | H | CH$_2$OH | |
| H | H | H | 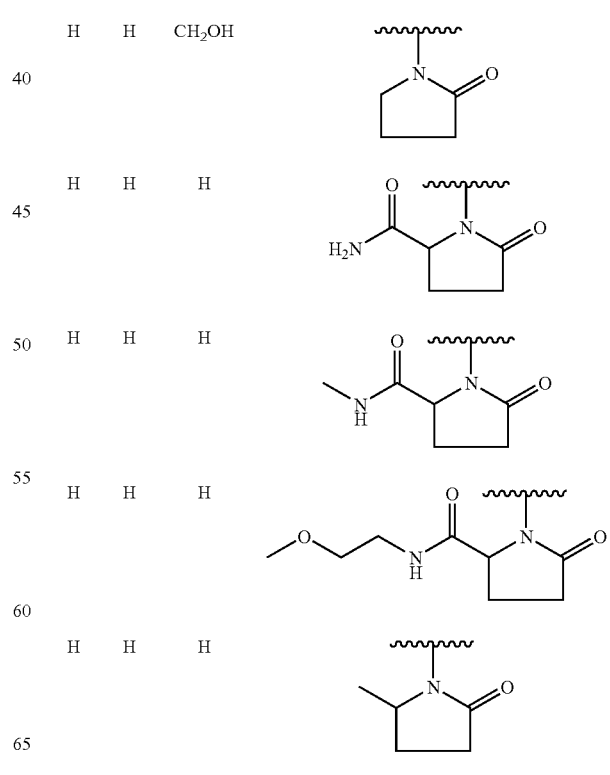 |
| H | H | H | |
| H | H | H | |
| H | H | H | |

-continued

| R⁸ | R¹ | R² | —NR⁷R¹¹ |
|---|---|---|---|
| H | H | H | succinimide (N-linked) |
| H | H | H | 1,2,4-triazol-4-yl |
| H | H | H | 3-oxo-1,2,4-triazol-4-yl (N—NH) |

12. The compound of claim 11 or the pharmaceutically acceptable salt or solvate thereof, wherein R¹, R², R⁷ R⁸ and R¹¹ are selected from the group consisting of

| R⁸ | R¹ | R² | —NR⁷R₁₁ |
|---|---|---|---|
| H | H | H | 2-oxopyrrolidin-1-yl |
| H | H | H | 2-oxoimidazolidin-1-yl (NH) |
| H | H | CH₃ | 2-oxopyrrolidin-1-yl |
| H | H | CH₂OH | 2-oxopyrrolidin-1-yl |
| H | H | H | 3-oxo-1,2,4-triazol-4-yl (N—NH) |

13. The compound of claim 12 having the formula:

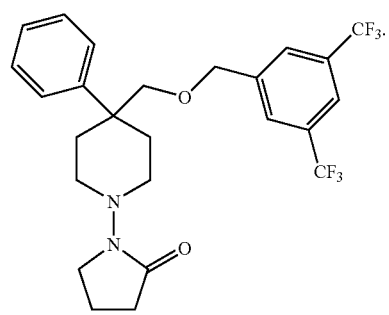

14. The compound of claim 12 having the formula:

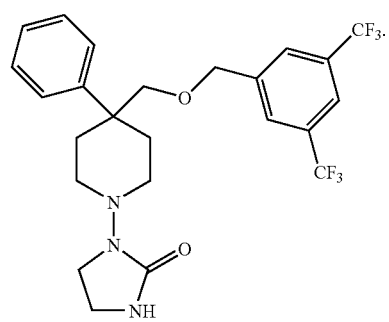

15. The compound of claim 12 having the formula:

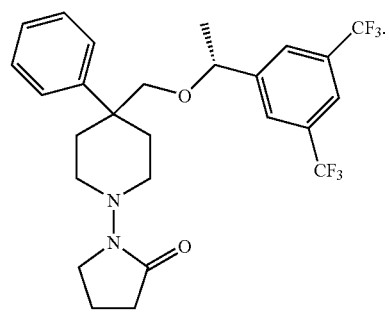

16. The compound of claim 12 having the formula:

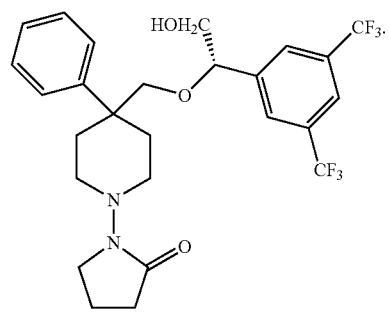

17. The compound of claim 12 having the formula:

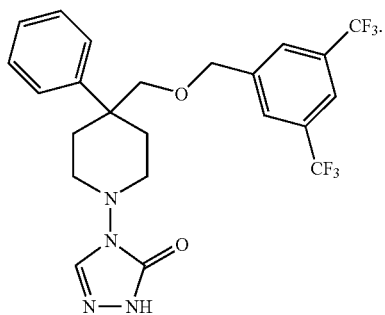

18. A pharmaceutical composition comprising a therapeutically effective amount of at least one compound of claim 1, and a pharmaceutically acceptable carrier.

19. A method for treating emesis, depression, anxiety or cough in a patient in need of such treatment comprising administering to said patient an effective amount of at least one compound of claim 1.

20. A method for treating emesis and/or nausea in a patient in need of such treatment comprising administering to said patient an effective amount of at least one compound of claim 1, in combination with an effective amount of ondansetron and/or with an effective amount of dexamethasone.

* * * * *

UNITED STATES PATENT AND TRADEMARK OFFICE
CERTIFICATE OF CORRECTION

PATENT NO. : 7,041,682 B2
APPLICATION NO. : 10/612176
DATED : May 9, 2006
INVENTOR(S) : Neng-Yang Shih It is certified that error appears in the above-identified patent and that said Letters Patent is hereby corrected as shown below:

Claim 1, Column 62, line 44: Replace "$C_3$-$C_8$" with -- $C_3$-$C_6$ --.

Claim 1, Column 63, line 19: Replace "$C_1$-$C_5$" with -- $C_1$-$C_6$ --.

Claim 1, Column 63, line 20: Replace "($C_3$-$C_{5\ cycloalkyl}$), -$NR^{13}$" with -- ($C_3$-$C_8$ cycloalkyl), -$NR^{13}$ --.

Claim 1, Column 64, line 13: Replace "-$SO^2$-" with -- -$SO_2$- --.

Claim 1, Column 64, line 21: Replace "$^{-NR21}$" with -- -$NR^{21}$ --.

Claim 1, Column 64, line 30: Replace "$(R^{19})^{n7}$" with -- $(R^{19})_{n7}$ --.

Claim 1, Column 64, line 39: Replace "$C_1$-$C_8$" with -- $C_1$-$C_6$ --.

Claim 1, Column 64, line 46: Replace "-$COOR^2$" with -- -$COOR^{12}$ --.

Claim 1, Column 64, line 50: Replace "$C_{1-C6}$" with -- $C_1$-$C_6$ --.

Claim 1, Column 64, line 51: Replace "heterocyclalkyl" with -- heterocycloalkyl --.

Claim 3, Column 65, line 42: Replace "$Ar_1$" with -- $Ar^1$ --.

Claim 8, Column 66, line 24: Replace "$R^{5\ and\ R6}$" with -- $R^5$ and $R^6$ --.

Claim 10, Column 66, line 54: Replace "$R^1$" with -- $R^{11}$ --.

UNITED STATES PATENT AND TRADEMARK OFFICE
CERTIFICATE OF CORRECTION

PATENT NO. : 7,041,682 B2
APPLICATION NO. : 10/612176
DATED : May 9, 2006
INVENTOR(S) : Neng-Yang Shih It is certified that error appears in the above-identified patent and that said Letters Patent is hereby corrected as shown below:

Claim 10, Column 69, Line 55: Insert 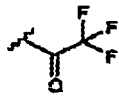

Claim 11, Column 71, Line 38: Replace "$R^1$" (second occurrence) with -- $R^{11}$ --.

Claim 12, Column 73, Line 33: Replace "-$NR^7R_{11}$" with -- -$NR^7R^{11}$ --.

Signed and Sealed this

Twenty-first Day of November, 2006

JON W. DUDAS
*Director of the United States Patent and Trademark Office*